(12) United States Patent
Astier et al.

(10) Patent No.: US 9,182,369 B2
(45) Date of Patent: Nov. 10, 2015

(54) MANUFACTURABLE SUB-3 NANOMETER PALLADIUM GAP DEVICES FOR FIXED ELECTRODE TUNNELING RECOGNITION

(71) Applicant: International Business Machines Corporation, Armonk, NY (US)

(72) Inventors: Yann Astier, White Plains, NY (US); Jingwei Bai, Los Angeles, CA (US); Michael A. Guillorn, Yorktown Heights, NY (US); Satyavolu S. Papa Rao, Poughkeepsie, NY (US); Joshua T. Smith, Croton on Hudson, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 13/921,383

(22) Filed: Jun. 19, 2013

(65) Prior Publication Data

US 2014/0374694 A1    Dec. 25, 2014

(51) Int. Cl.
*G01N 27/414* (2006.01)
*H01L 29/41* (2006.01)
*G01N 33/487* (2006.01)

(52) U.S. Cl.
CPC ...... *G01N 27/4145* (2013.01); *G01N 33/48721* (2013.01); *H01L 29/413* (2013.01)

(58) Field of Classification Search
CPC .................................................. H01L 29/413
See application file for complete search history.

(56) References Cited

U.S. PATENT DOCUMENTS

| | | |
|---|---|---|
| 4,576,829 A | 3/1986 | Kaganowicz et al. |
| 4,692,992 A | 9/1987 | Hsu |
| 5,671,086 A | 9/1997 | Parvin et al. |
| 6,180,490 B1 | 1/2001 | Vassiliev et al. |
| 6,217,872 B1 | 4/2001 | Okayama et al. |
| 6,413,792 B1 | 7/2002 | Sauer et al. |
| 6,582,926 B1 | 6/2003 | Chilkoti |
| 6,621,191 B1 | 9/2003 | Nomura et al. |
| 6,627,067 B1 | 9/2003 | Branton et al. |
| 6,727,174 B1 | 4/2004 | Kotecki et al. |
| 6,777,260 B1 | 8/2004 | Chen |
| 6,783,643 B2 | 8/2004 | Golovchenko et al. |
| 6,962,849 B1 | 11/2005 | Kamal et al. |
| 7,282,130 B2 | 10/2007 | Flory |
| 7,347,921 B2 | 3/2008 | Barth et al. |

(Continued)

FOREIGN PATENT DOCUMENTS

| | | |
|---|---|---|
| CN | 101203740 A | 6/2008 |
| CN | 101385126 A | 3/2009 |

(Continued)

OTHER PUBLICATIONS

U.S. Appl. No. 12/820,543, filed Jun. 22, 2012; First Named Inventor: Ali Afzali-Ardakani.

(Continued)

*Primary Examiner* — Yu-Hsi D Sun
(74) *Attorney, Agent, or Firm* — Cantor Colburn LLP

(57) ABSTRACT

A technique is provided for manufacturing a nanogap in a nanodevice. An oxide is disposed on a wafer. A nanowire is disposed on the oxide. A helium ion beam is applied to cut the nanowire into a first nanowire part and a second nanowire part which forms the nanogap in the nanodevice. Applying the helium ion beam to cut the nanogap forms a signature of nanowire material in proximity to at least one opening of the nanogap.

9 Claims, 19 Drawing Sheets

(56) References Cited

U.S. PATENT DOCUMENTS

| | | | |
|---|---|---|---|
| 7,351,648 B2 | 4/2008 | Furukawa et al. | |
| 7,468,271 B2 | 12/2008 | Golovchenko et al. | |
| 7,540,717 B2 | 6/2009 | Sheng et al. | |
| 7,553,730 B2 | 6/2009 | Barth et al. | |
| 7,560,141 B1 | 7/2009 | Kim et al. | |
| 7,582,490 B2 | 9/2009 | Golovchenko et al. | |
| 7,846,738 B2 | 12/2010 | Golovchenko et al. | |
| 2004/0229386 A1 | 11/2004 | Golovchenko et al. | |
| 2005/0019784 A1 | 1/2005 | Su et al. | |
| 2005/0026238 A1 | 2/2005 | Berndt | |
| 2005/0101100 A1 | 5/2005 | Kretchmer et al. | |
| 2005/0110990 A1 | 5/2005 | Koo et al. | |
| 2005/0158763 A1 | 7/2005 | Ivanisevic et al. | |
| 2005/0202446 A1 | 9/2005 | Yang et al. | |
| 2006/0105553 A1 | 5/2006 | Wellhausen | |
| 2006/0154399 A1 | 7/2006 | Sauer et al. | |
| 2006/0154400 A1 | 7/2006 | Choi et al. | |
| 2006/0169588 A1 | 8/2006 | Jacobson et al. | |
| 2006/0180469 A1 | 8/2006 | Han et al. | |
| 2006/0246497 A1 | 11/2006 | Huang et al. | |
| 2006/0275778 A1* | 12/2006 | Wu et al. ............... | 435/6 |
| 2007/0020146 A1 | 1/2007 | Young et al. | |
| 2007/0042366 A1 | 2/2007 | Ling | |
| 2007/0048745 A1 | 3/2007 | Joyce et al. | |
| 2007/0138132 A1 | 6/2007 | Barth | |
| 2007/0187694 A1 | 8/2007 | Pfeiffer | |
| 2007/0190542 A1 | 8/2007 | Ling et al. | |
| 2008/0003571 A1 | 1/2008 | McKernan et al. | |
| 2008/0032290 A1 | 2/2008 | Young | |
| 2008/0102504 A1 | 5/2008 | Akeson et al. | |
| 2008/0105539 A1 | 5/2008 | Lyding et al. | |
| 2008/0119366 A1 | 5/2008 | Sauer et al. | |
| 2008/0171316 A1 | 7/2008 | Golovchenko et al. | |
| 2008/0187915 A1 | 8/2008 | Polonsky et al. | |
| 2008/0257859 A1 | 10/2008 | Golovchenko et al. | |
| 2009/0136958 A1 | 5/2009 | Gershow et al. | |
| 2009/0188794 A1 | 7/2009 | Simon et al. | |
| 2009/0221443 A1 | 9/2009 | Heller et al. | |
| 2009/0222216 A1 | 9/2009 | Hibbs et al. | |
| 2009/0295372 A1 | 12/2009 | Krstic et al. | |
| 2010/0009134 A1 | 1/2010 | Drndic et al. | |
| 2010/0025249 A1 | 2/2010 | Polonsky et al. | |
| 2010/0032302 A1 | 2/2010 | Holtermann et al. | |
| 2010/0084276 A1 | 4/2010 | Lindsay | |
| 2010/0142259 A1 | 6/2010 | Drndic et al. | |
| 2010/0144535 A1 | 6/2010 | Strachan et al. | |
| 2010/0327255 A1 | 12/2010 | Peng et al. | |
| 2010/0327847 A1 | 12/2010 | Leiber et al. | |
| 2010/0331194 A1 | 12/2010 | Turner et al. | |
| 2011/0052813 A1 | 3/2011 | Ho et al. | |
| 2011/0085759 A1 | 4/2011 | Lee et al. | |
| 2011/0120868 A1 | 5/2011 | Lindsay et al. | |
| 2011/0220574 A1 | 9/2011 | Bakajin et al. | |
| 2011/0236984 A1 | 9/2011 | Sun et al. | |
| 2011/0268647 A1 | 11/2011 | Ivanovici et al. | |
| 2011/0279125 A1 | 11/2011 | Bedell et al. | |
| 2012/0146162 A1 | 6/2012 | Cho et al. | |
| 2012/0193235 A1 | 8/2012 | Afzali-Ardakani et al. | |
| 2012/0193236 A1 | 8/2012 | Peng et al. | |
| 2012/0193237 A1 | 8/2012 | Afzali-Ardakani et al. | |
| 2012/0288948 A1 | 11/2012 | Lindsay et al. | |
| 2013/0037410 A1 | 2/2013 | Xu et al. | |
| 2013/0203050 A1 | 8/2013 | Huber et al. | |
| 2013/0265031 A1 | 10/2013 | Shim et al. | |

FOREIGN PATENT DOCUMENTS

| | | |
|---|---|---|
| EP | 0261592 A1 | 9/1987 |
| EP | 1441213 | 7/2004 |
| EP | 1486775 A | 12/2004 |
| WO | WO0181908 A | 11/2001 |
| WO | WO2006122317 | 11/2006 |
| WO | WO2007084163 A | 7/2007 |
| WO | WO2008051308 A2 | 5/2008 |
| WO | WO2008132643 A1 | 11/2008 |
| WO | WO2009020682 A2 | 2/2009 |
| WO | WO2009032756 A2 | 3/2009 |
| WO | WO2009117522 A2 | 9/2009 |

OTHER PUBLICATIONS

U.S. Appl. No. 13/248,176; Title: Selective Placement of Carbon Nanotubes via Coulombic Attraction of Oppositely Charged Carbon Nonotubes and Self-Assembled Monolayers; filed Sep. 29, 2011; First Named Inventor: Ali Afzali-Ardakani.

Hongbo Peng, et al., Pending U.S. Appl. No. 13/359,729, entitled "Electron Beam Sculpting of Tunneling Junction for Nanopore DNA Sequencing," filed with the U.S. Patent and Trademark Office of Jan. 27, 2012.

Hongbo Peng, et al., Pending U.S. Appl. No. 13/359,729, entitled "Electron Beam Sculpting of Tunneling Junction for Nanopore DNA Sequencing," filed with the U.S. Patent and Trademark Office on Jan. 27, 2012.

Hongbo Peng, et al., Pend U.S. Appl. No. 13/359,743, entitled "DNA Motion Control Based on Nanopore with Organic Coating Forming Transient Bonding to DNA," filed with the U.S. Patent and Trademark Office on Jan. 27, 2012.

Hongbo Peng, et al., Pending U.S. Appl. No. 13/359,750, entitled "DNA Sequencing Using Multiple Metal Layer Structure with Organic Coatings Transient Bonding to DNA Bases," filed with the U.S. Patent and Trademark Office on Jan. 27, 2012.

Hong Peng, et al., Pending U.S. Appl. No. 13/359,766, entitled "DNA Sequencing Using Multiple Metal Layer Structure with Different Organic Coatings Forming Different Transient Bondings to DNA," filed with the U.S. Patent and Trademark Office on Jan. 27, 2012.

A. Bergvall et al., "Graphene nanogap for gate-tunable quantum-coherent single-molecule electronics," Phys. Rev. B, vol. 84, No. 15, 2011, 155451, 7 pages.

A. J. Storm et al., "Fabrication of solid-state nanopores with single-nanometre precision," Nature Materials, vol. 2, Aug. 2003, pp. 537-540.

Amit Meller et al., "Rapid nanopore discrimination between single polynucleotide molecules," PNAS, Feb. 1, 2000, vol. 97, No. 3, pp. 1079-1084.

Akeson, Mark, et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77, Dec. 1999, pp. 3227-3233.

Branton, Daniel, et al., "The potential and challenges of nanopore sequencing" NIH Public Access—Author Manuscript, Nat Biotechnol. available in PMC May 18, 2009, pp. 1-17.

Gracheva, Maria E. et al., "Simulation of the electric response of DNA translocation through a semiconductor nanopore—capacitor", Institute of Physics Publishing, Nanotechnology, vol. 17 (2006), pp. 622-633.

Heng, Jiunn B. et al., "Sizing DNA Using a Nanometer-Diameter Pore", Biophysical Journal, vol. 87, Oct. 2004, pp. 2905-2911.

Kasianowicz, John J., et al., "Characterization of individual polynucleotide molecules using a membrane channel", Proc. Natl. Acad. Sci. USA, vol. 93, Nov. 1996, pp. 13770-13773.

Lagerqvist, Johan et al., "Fast DNA Sequencing via Transverse Electronic Transport", Nano Lett., vol. 6, No. 4, revised Manuscript Received Mar. 1, 2006, pp. 779-782.

Soni, Gautam V. et al., "Progress toward Ultrafast DNA Sequencing Using Solid-State Nanopores", Clinical Chemistry, vol. 53, No. 11, (2007), pp. 1-6.

Douville, et al., "DNA Linearization Through Confinement in Nanofluidic Channels, Anal Bioanal Chem.", Aug. 2008; vol. 391; No. 7; pp. 2395-2409; Abstract; p. 2402, col. 2; para 5; p. 2406; col. 2; para 2; p. 2407; Fig. 5b.

B. Luan et al., "Tribological Effects on DNA Translocation in a Nanochannel Coated with a Self-Assembled Monolayer," J. Phys. Chem. B, vol. 114, 2010, pp. 17172-17176; Nov. 12, 2010.

Bae, S. et al., "Roll-to-Roll Production of 30-inch Graphene Films for Transparent Electrodes," Nature Nanotechnology, Published online: Jun. 20, 2010, 5 pages.

(56) References Cited

OTHER PUBLICATIONS

D. Branton et al., "The Potential and Challenges of Nanopore Sequencing," Nat. Biotech., vol. 26 (10), pp. 1146-1153 Author Manuscript (Oct. 2008); 17 pages.

I. Braslavsky, B. Hebert, E. Kartalov, S. R. Quake, "Sequence Information Can Be Obtained from Single DNA Molecules," Proc. Natl. Acad. Sci. USA, vol. 100, pp. 3960-3964 (2003).

S. Chang et al., "Chemical recognition and binding kinetics in a functionalized tunnel junction," Nanotechnology, vol. 23, No. 23, 2012, 235101, 14 pages.

S. Chang et al., "Electronic signatures of all four DNA nucleosides in a tunneling gap," Nano Letters, vol. 10, No. 3, 2010, pp. 1070-1075.

F. S. Collins, M. Morgan, A. Patrinos, "The Human Genome Project—Lessons From Large-scale Biology," Science, vol. 300, pp. 286-290 (2003).

D.W. Hess, "Plasma-assisted oxidation, anodization, and nitridation of silicon," IBM J. Res. Develop. vol. 43. No. 1/2, Jan./Mar. 1999, pp. 127-145.

M. Fedurco, A. Romieu, S. Williams, I. Lawrence, G. Turcatti, "BTA, a Novel Reagent for DNA Attachment on Glass and Efficient Generation of Solid-phase Amplified DNA Colonies," Nucleic Acids Res. vol. 34, pp. e22 (2006).

A. K. Geim and K. S. Novoselov, "The Rise of Graphene," Nature Materials 6, 183 (2007), 9 pages.

S. Harrer et al. "Electrochemical Characterization of Thin Film Electrodes Towards Developing a DNA-Transistor," Langmuir, vol. 26 (24), pp. 19191-19198 (2010).

S. Harrer et al., "Electrochemical Protection of Thin Film Electrodes in Solid State Nanopore," Nanotechnology, vol. 22, 2011, 275304, 6 pages.

T. D. Harris et al., "Single-molecule DNA Sequencing of a Viral Genome," Science, vol. 320, pp. 106-109 (2008).

Novoselov K S et al, "Electric Field Effect in Atomically Thin Carbon Films" Science, American Association for the Advancement of Science, US, Washington, DC, vol. 306, No. 5696, Oct. 11, 2004, pp. 666-669, XP009086357, ISSN: 0036-8075, the whole document.

Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.

Polonsky et al., "Nanopore in metal-dielectric sandiwch for DNA position control," Applied Physics Letters 91, 153103 (2007).

S. Roy et al., "Direct Electrical Measurements on Single-Molecule Genomic DNA Using Single-Walled Carbon Nanotubes," Nano Letters, vol. 8, No. 1, 2008, pp. 26-30.

F. Sanger, S. Nicklen, A. R. Coulson, "DNA sequencing with chain termination inhibitors," Proc. Natl. Acad. Sci USA., vol. 74 (12), pp. 5463-5467 (1977).

Schedin F et al: "Detection of Individual Gas Molecules Absorbed on Graphene" Nature Materials Nature Publishing Group, UK, vol. 6, No. 9, Sep. 2007, pp. 652-655, XP002506772, ISSN: 1476-1122, the whole document.

J. Shedure et al., "Accurate Multiplex Polony Sequencing of an Evolved Bacterial Genome," Science, vol. 309, pp. 1728-1732 (2005).

A. Sidorenko et al., "Controlled Switching of the Wetting Behavior of Bioimetic Surfaces with Hydrogel-Supported Nanostructures," J. Mater. Chem., vol. 18, 2008, pp. 3841-3846.

Soni G and Meller A, "Progress Towards Ultrafast Dna Sequencing Using Solid State Nanopores," Clin. Chem. Jan. 3, 1996 (2007), 6 pages.

Eric Stern, James F. Klemic, David A. Routenberg, Pauline N. Wyrembak, Daniel B. Turner-Evans, Andrew D. Hamilton, David A. Lavan, Tarek M. Fahmy and Mark A. Reed, "Label-free immunodetection with CMOS-compatible semiconducting nanowires," Nature Publishing Group, vol. 445, Feb. 2007, doi:10. 1038/nature05498, pp. 1-4.

A. J. Storm, J. H. Chen, X. S. Ling, H. W. Zandbergen and C. Dekker, "Fabrication of Solid-State Nanopores with Single-Nanometre Precision," Nature Materials 2, 537-540 (2003).

G. Tizazu et al., "Photopatterning, Etching, and Derivatization of Self-Assembled Monolayers of Phosphonic Acids on the Native Oxide of Titanium," Langmuir, vol. 25, 2009, pp. 10746-10753.

M. Tsutsui et al., "Identifying single nucleotides by tunnelling current," Nature Nanotechnology, vol. 5, 2010, pp. 286-290.

G. Turcatti, A. Romieu, M. Fedurco, A. P. Tairi, "A New Class of Cleavable Fluorescent Nucleotides: Synthesis and Optimization as Reversible Terminators for DNA Sequencing by Synthesis," Nucleic Acids Res., vol. 36, pp. e25 (2008).

U.S. Appl. No. 12/820,543, filed Jun. 22, 2010; Title: Forming an Electrode Having Reduced Corrosion and Water Decomposition on Surface Using an Organic Protective Layer; Harrer et al.

S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-Institute for Biochemistry.

G. Wang et al., "Photon Gated Transport at the Glass Nanopore Electrode," J. Am. Chem. Soc., vol. 128, 2006, pp. 13553-13558.

B. Luan et al., "DNA-translocation through a solid state nanopore coated with a self-assembled monolayer," Bull. Am. Phys. Soc., APS March Meeting 2011, vol. 56, No. 1, Abstract V43.00002, Mar. 24, 2011, 1 page.

Written Opinion of the International Searching Authority; date of mailing Apr. 5, 2011; pp. 1-6; International application No. PCT/US11/23872.

J. Hass, W.A. De Heer and E.H. Conrad, "The Growth and Morphology of Epitaxial Multilayer Graphene," Journal of Physics: Condensed Matter 20, 323202 (2008), 28 pages.

Heng J B, Ho C, Kim T, Timp R, Aksimentiev A, Grinkova Y V, Sligar S, Schulten K and Timp G, "Sizing DNA Using a Nanometer-diameter Pore," Biophys Journal vol. 87, 2905-2911 (Oct. 2004); 7 pages.

H.W.C. Postma, "Rapid Sequencing of Individual DNA Molecules in Graphene Nanogaps," Nano Letters, vol. 10, No. 2, Jan. 4, 2010, pp. 420-425.

Notice of Allowance dated Aug. 22, 2011 for U.S. Appl. No. 12/704,665, filed Feb. 12, 2010; 13 pages.

International Search Report—PCT; Notification of Transmittal of the International Search Report and the Written Opinion of the International Searching Authority, or the Declaration; Apr. 5, 2011; International application No. PCT/US1123872.

A. P. Ivanov et al., "DNA tunneling detector embedded in a nanopore," Nano Letters, vol. 11, No. 1, Jan. 12, 2011, pp. 279-285.

J. Prasongkit et al., "Transverse conductance of DNA necleotides in a graphene nanogap from first principles," arXiv:1012.1669v2 [physics.ins-det], [v1] Dec. 8, 2010, [v2] Jan. 14, 2011, Nano Lett., vol. 11, No. 5, 2011, pp. 1941-1945.

T. Kiefer et al., "A single nanotrench in a palladium microwire for hydrogen detection," Nanotechnology, vol. 19, No. 12, 2008, 125502, 9 pages.

K.S. Kim, Y. Zhao, H. Jang, S. Y. Lee, J. M. Kim, K. S. Kim, J. H. Ahn, P. Kim, J. Y. Choi, B. H. Hong, "Large-Scale Pattern Growth of Graphene Films for Stretchable Transparent Electrodes," Nature 457, 706-710 (2009).

J. Li et al., "Ion-beam sculpting at nanometre length scales," Nature, vol. 412, 2001, pp. 166-169.

B. Luan, H. Peng, S. Polonsky, S. Rossnagel, G. Stolovitzky, and G. Martyna, "Base-by-base Ratcheting of Single-stranded DNA Through a Solid-state Nanopore," Phys. Rev. Lett., vol. 104 (23) pp. 238103-1-238103-4 (2010).

B. Luan, A. Aksimentiev, "Control and Reversal of the Electrophoretic Force on DNA in a Charged Nanopore," J. Phys. Condens. Matter, vol. 22, pp. 454123 (2010).

B. Luan et al., "Tribological Effects on DNA Translocation in a Nanochannel Coated with a Self-Assembled Monolayer," J. Phys. Chem. B, vol. 114, 2010, pp. 17172-17176.

(56) References Cited

OTHER PUBLICATIONS

M. J. Kim et al., "Rapid Fabrication of Uniformly Sized Nanopores and Nanopore Arrays for Parallel DNA Analysis," Adv. Mater. 2006, 18, pp. 3149-3153.

M. Margulies et al., "Genome Sequencing in Mircrofabricated High-density Pico-litre Reactors," Nature, vol. 437, pp. 376-380 (2005).

Meller A., Nivon L., Brandin E., Golovchenko J. and Branton D., "Rapid Nanopore Discrimination Between Signle Polynucleotide Molecules," Proc. Natl Acad. Sci. USA 97 1079-84 (2000).

T. Nagase et al., "Maskless fabrication of nanogap electrodes by using Ga-focused ion beam etching." Journal of Micro/Nanolithography, MEMS, and MOEMS, vol. 5, No. 1, 2006, 011006, 6 pages.

United States Patent and Trademark Office, Non-Final Office Action for U.S. Appl. No. 12/704,665 pp. 1-15.

G. Sigalov, et al., "Detection of DNA Sequences Using an Alternating Electric Field in a Nanopore Capacitor," Nano Letters 2008, vol. 8, No. 1; pp. 56-63.

H. Stranneheim, et al., "Stepping Stones in DNA Sequencing," Biotechnical Journal (2012) 7 (9) pp. 1063-1073.

He, et al., "Identification of DNA Basepairing via Tunnel-Current Decay," Nano Letters 2007; vol. 7, No. 12; pp. 3854-3858.

Notification of Transmittal of the International Search Report and the Written Opinion of the International Searching Authority, or the Declaration; Mail date: Oct. 30, 2014; Int'l App. No. PCT/US14/37235; Int'l Filing Date: May 8, 2014; 16 pages.

\* cited by examiner

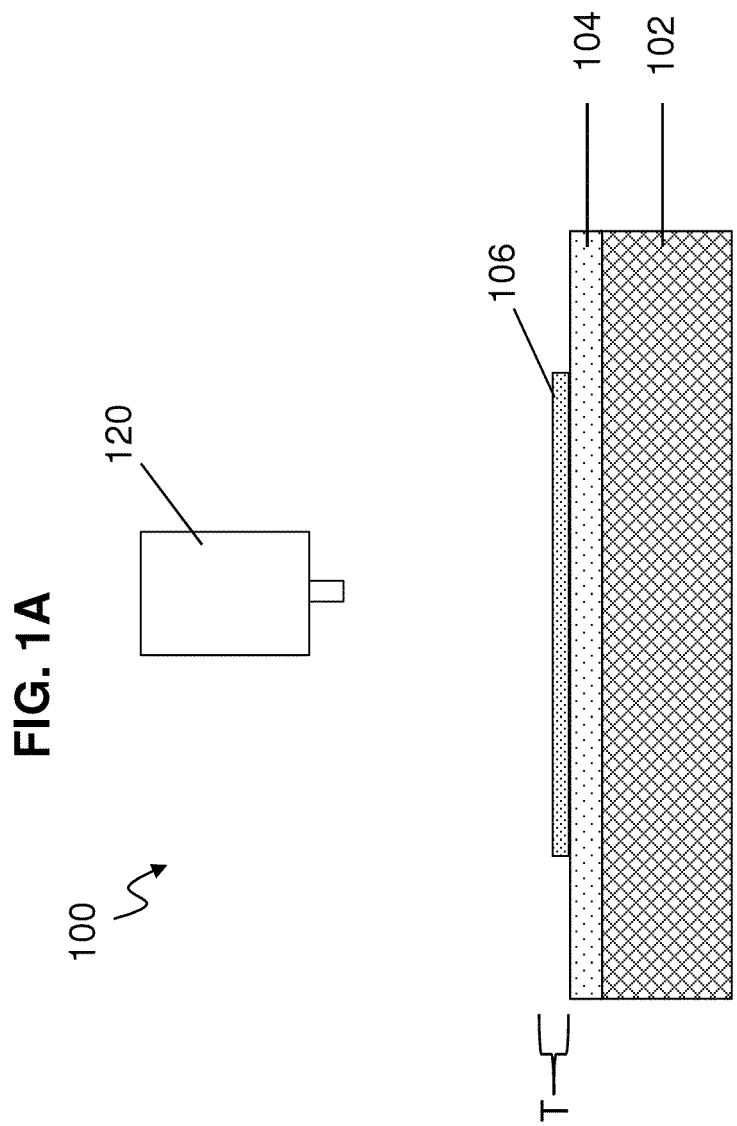

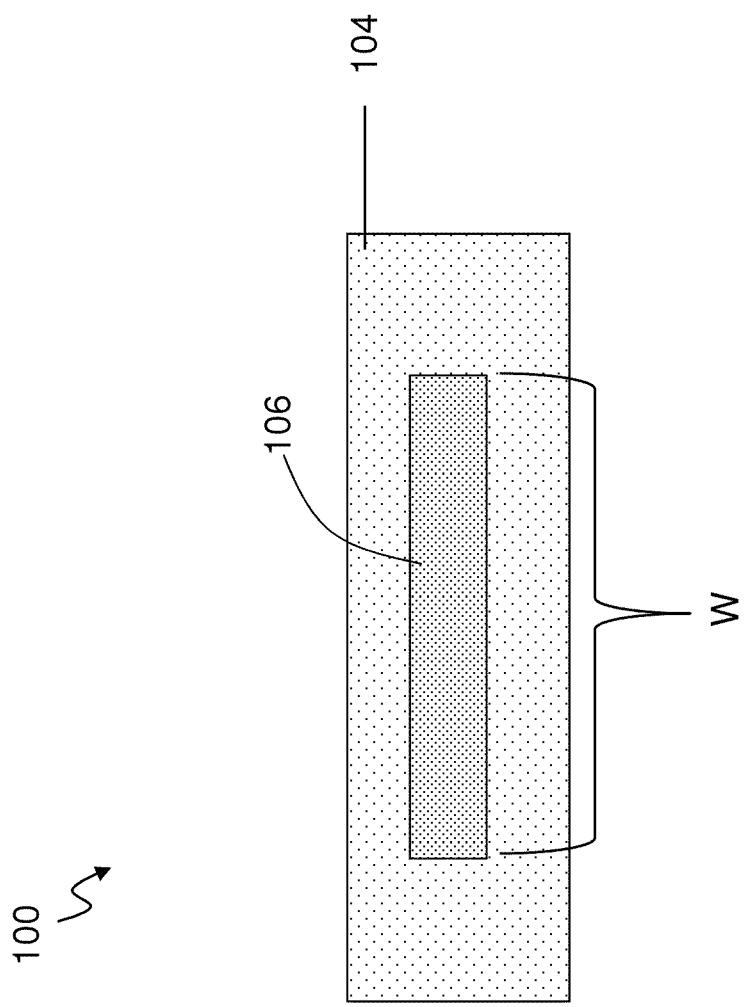

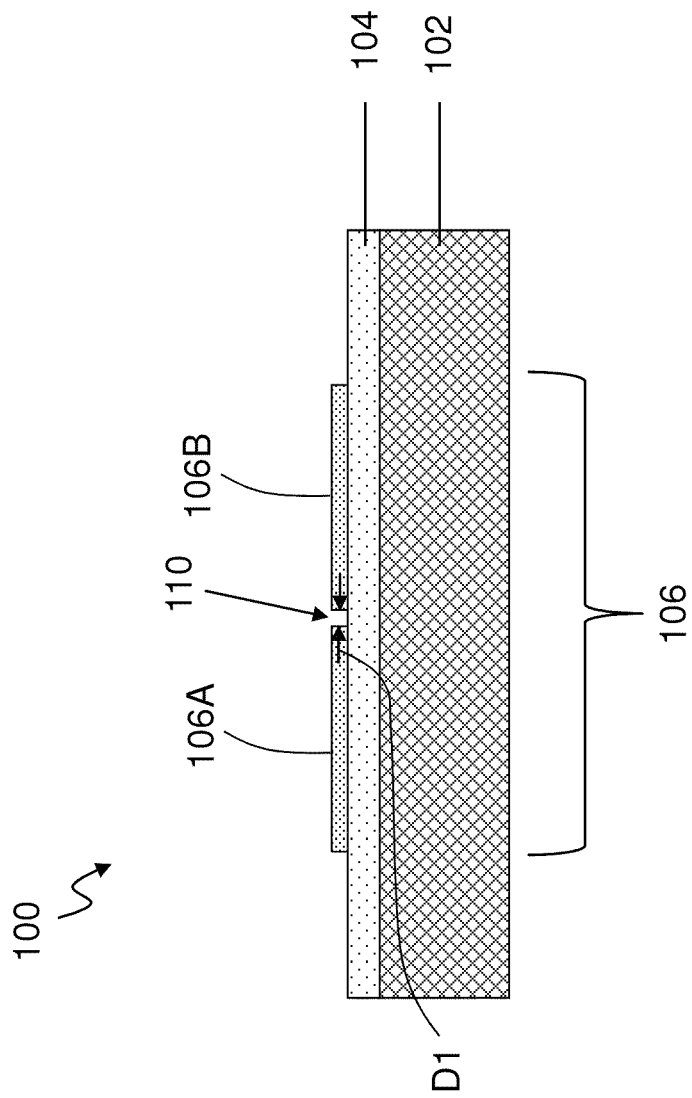

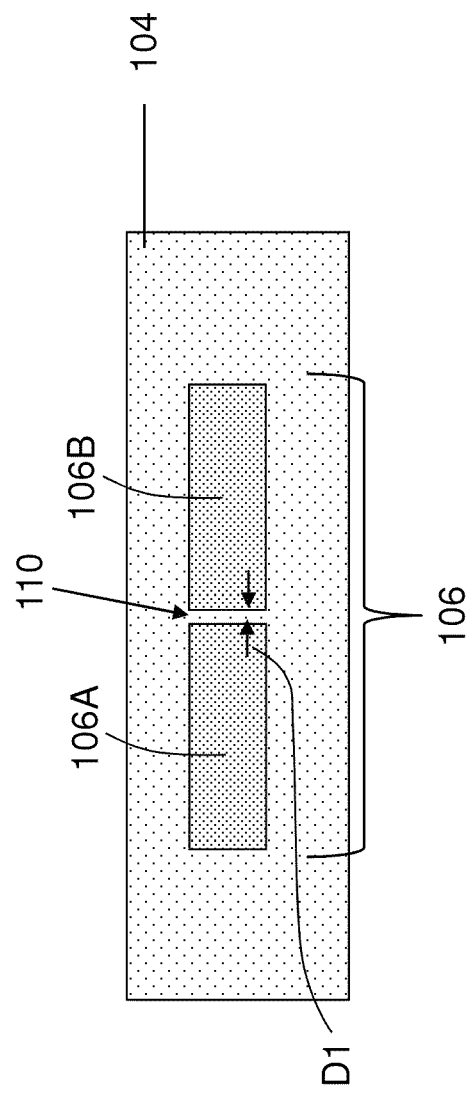

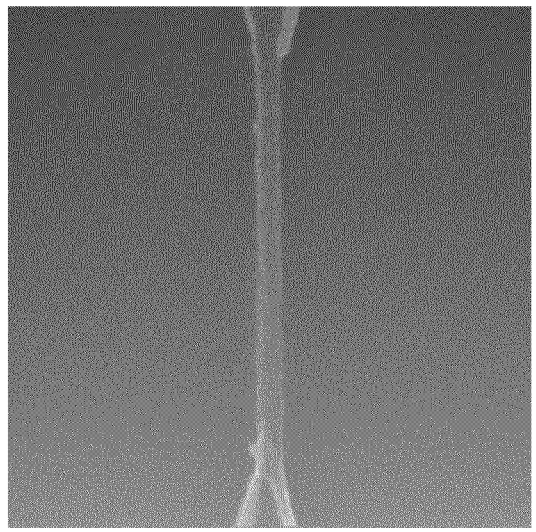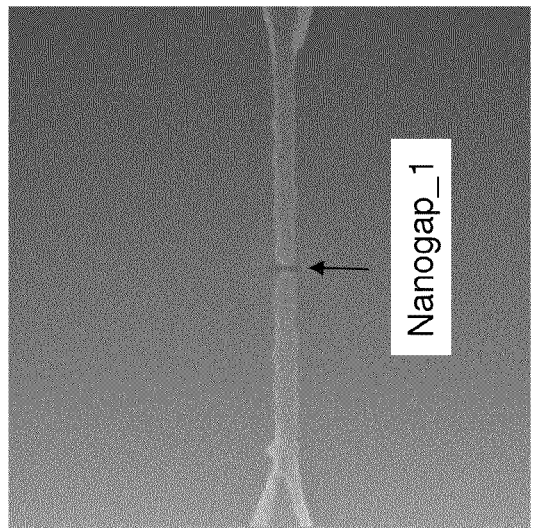
FIG. 2A
FIG. 2B

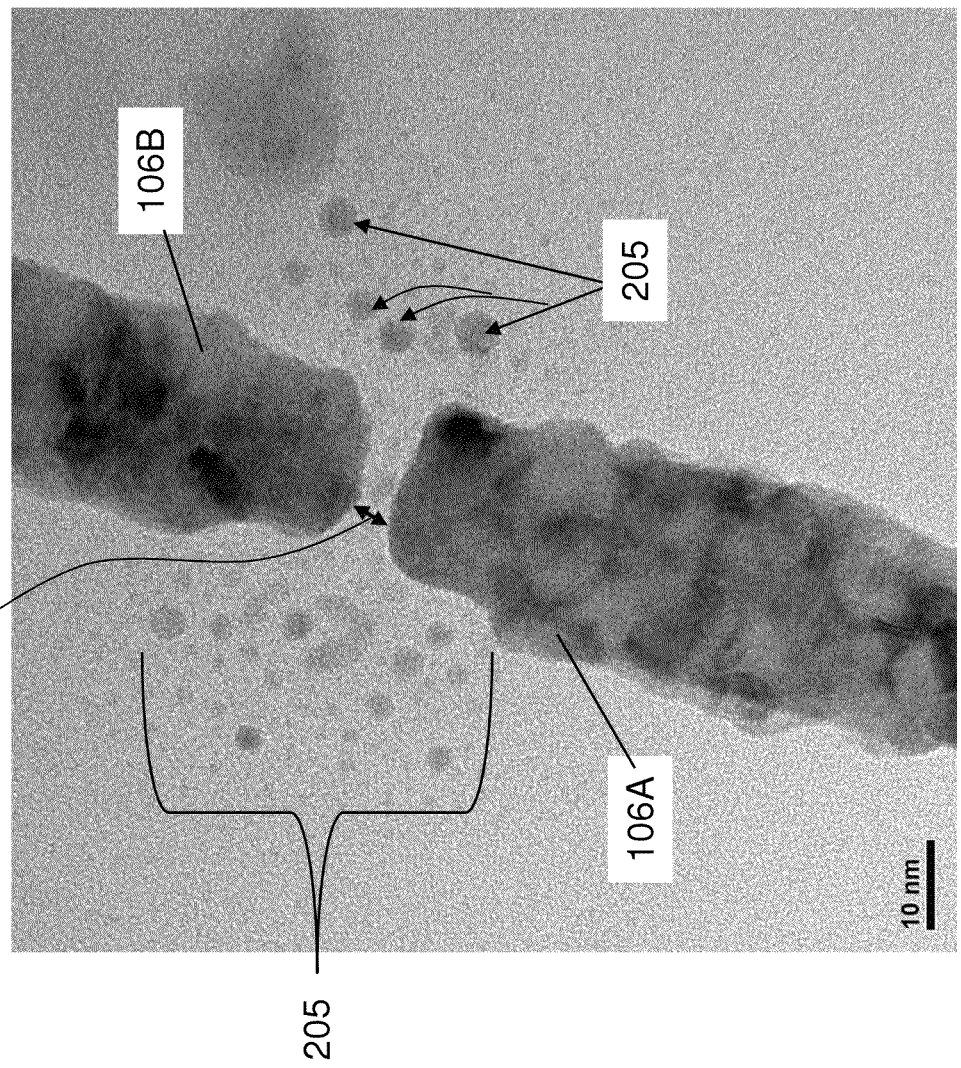

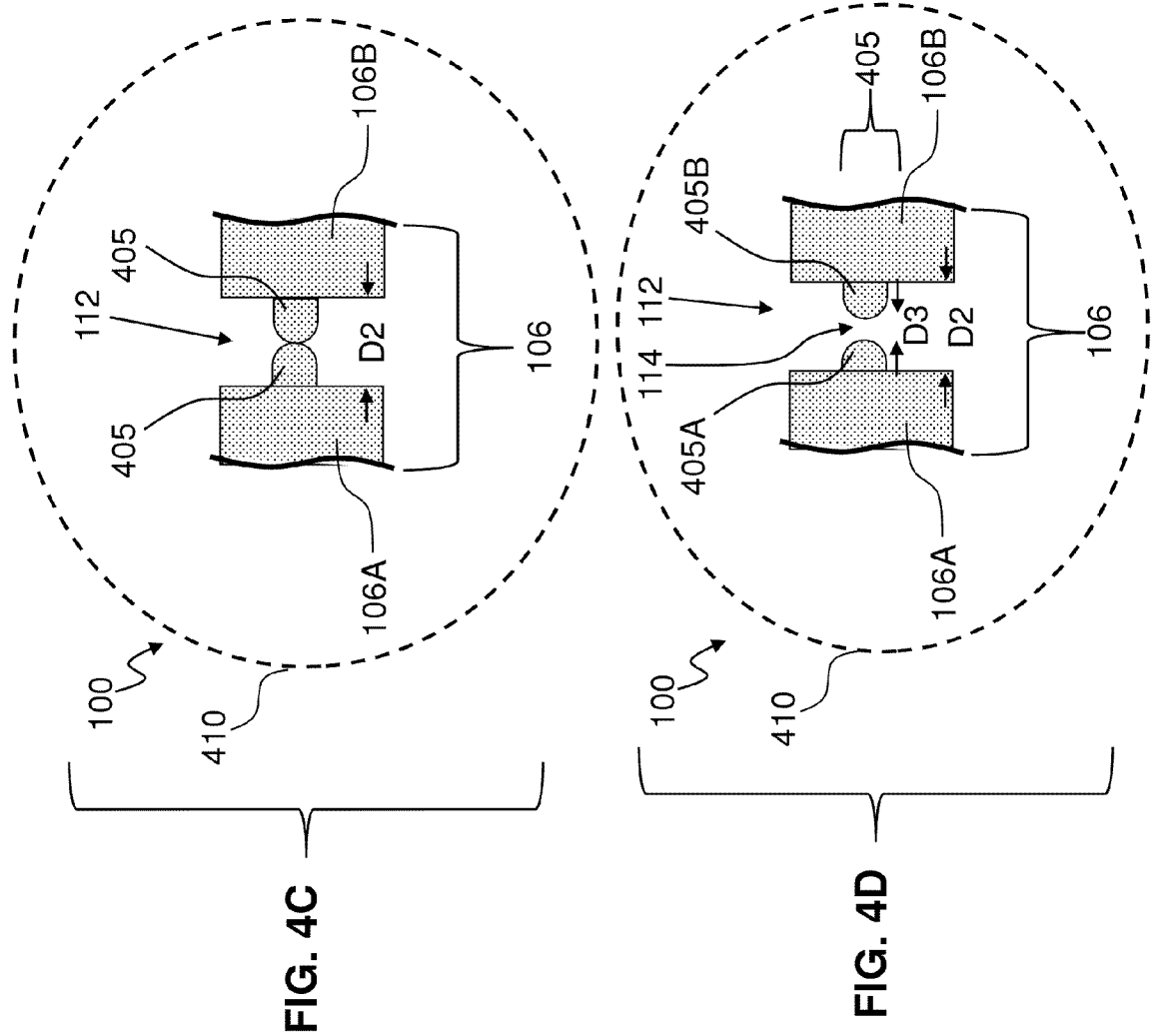

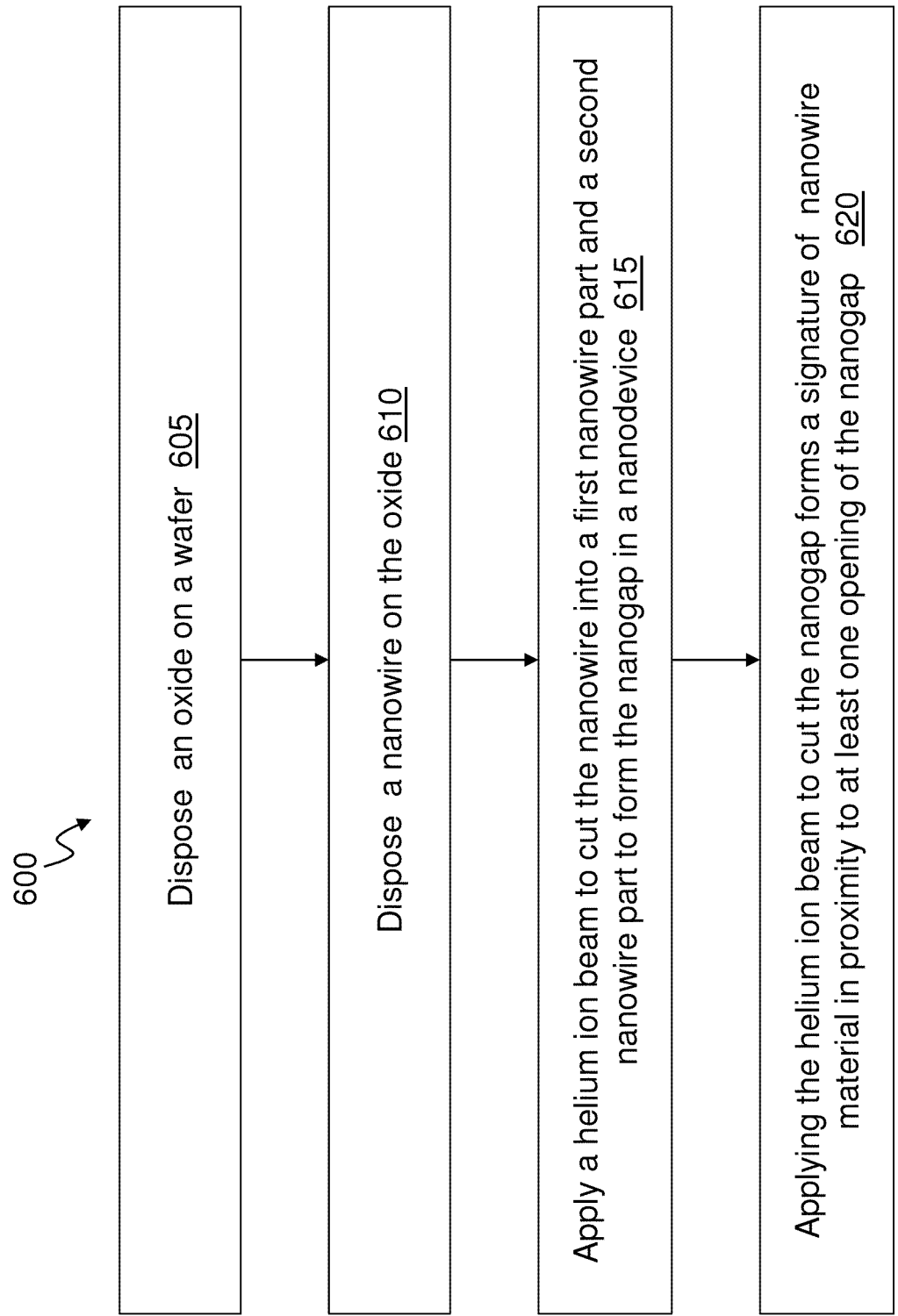

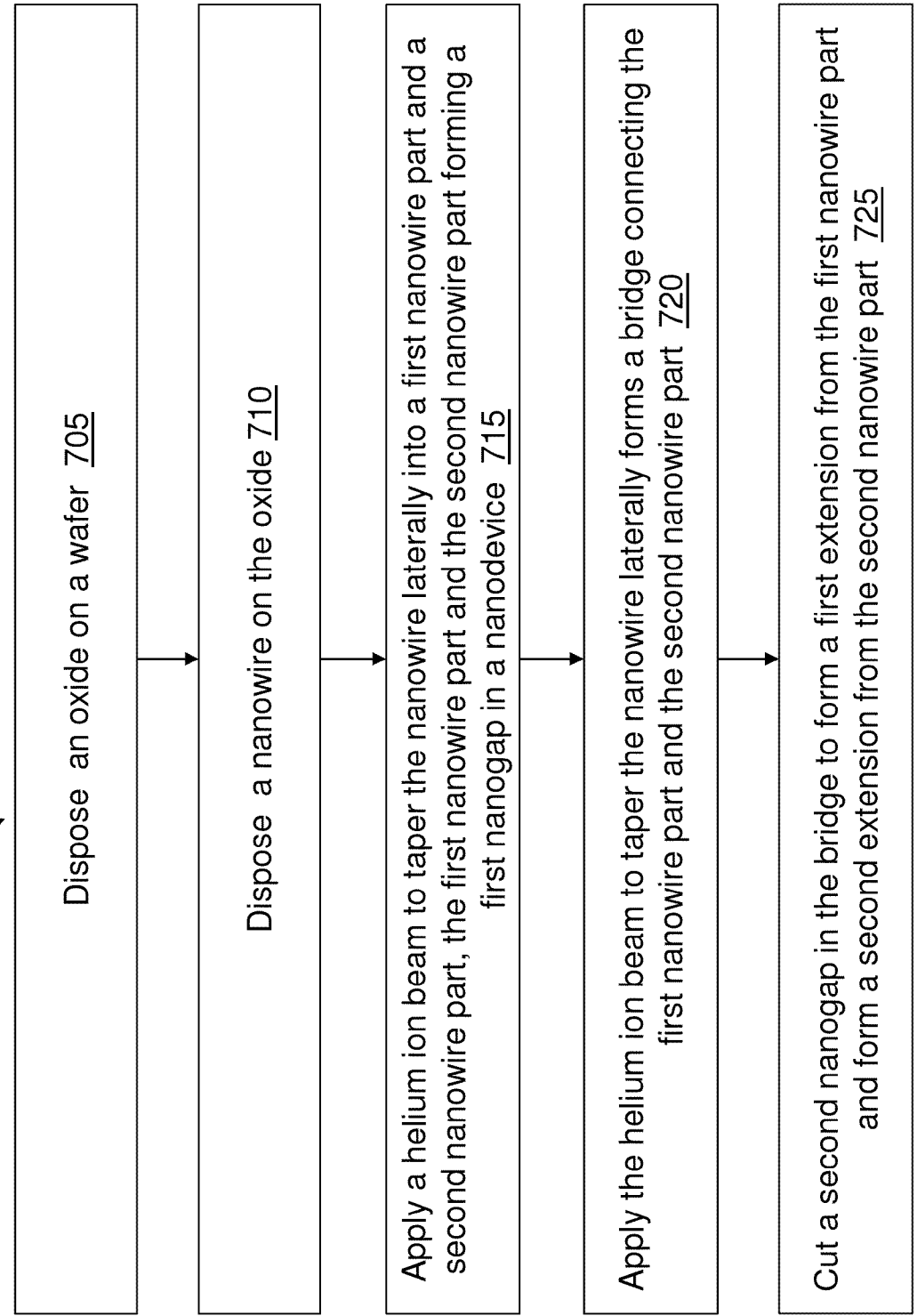

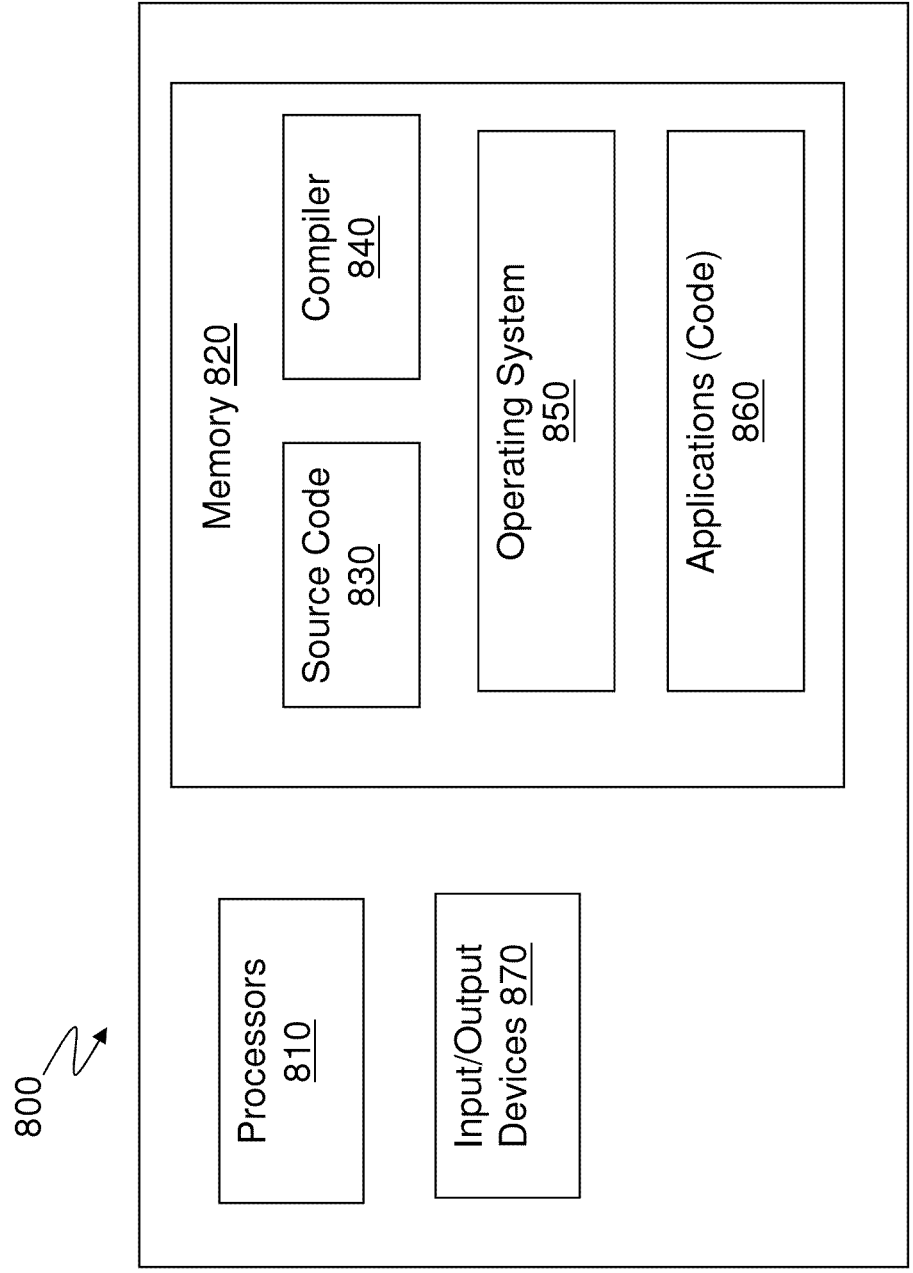

MANUFACTURABLE SUB-3 NANOMETER PALLADIUM GAP DEVICES FOR FIXED ELECTRODE TUNNELING RECOGNITION

BACKGROUND

The present invention relates generally to nanodevices, and more specifically, to manufacturing a sub-3 nanometer palladium nanogap.

Nanopore sequencing is a method for determining the order in which nucleotides occur on a strand of deoxyribonucleic acid (DNA). A nanopore (also referred to as pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to one embodiment, a method for manufacturing a nanogap in a nanodevice is provided. The method includes disposing an oxide on a wafer, disposing a nanowire on the oxide, and applying a helium ion beam to cut the nanowire into a first nanowire part and a second nanowire part to form the nanogap in the nanodevice. Applying the helium ion beam to cut the nanogap forms a signature of nanowire material in proximity to at least one opening of the nanogap.

According to one embodiment, a method for manufacturing a nanogap in a nanodevice is provided. The method includes disposing an oxide on a wafer, disposing a nanowire on the oxide, and applying a helium ion beam to taper the nanowire laterally into a first nanowire part and a second nanowire part. The first nanowire part and the second nanowire part form a first nanogap in the nanodevice. Applying the helium ion beam to taper the nanowire laterally forms a bridge connecting the first nanowire part and the second nanowire part. A second nanogap is cut in the bridge to form a first extension from the first nanowire part and form a second extension from the second nanowire part.

According to one embodiment, a structure utilized in sequencing. The structure includes an oxide on a wafer, a nanowire on the oxide, and a tapered lateral area of the nanowire from applying a helium ion beam. The tapered lateral area forms a first nanowire part and a second nanowire part, and the first nanowire part and the second nanowire part form a first nanogap. The tapered lateral area forms a bridge connecting the first nanowire part and the second nanowire part. A second nanogap in the bridge forms a first extension from the first nanowire part and forms a second extension from the second nanowire part.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 1A illustrates a cross-sectional view of a method of forming a nanodevice according to an embodiment.

FIG. 1B illustrates a top view of the nanodevice according to an embodiment.

FIG. 1C illustrates a cross-sectional view of a nanogap cut in a nanowire according to an embodiment.

FIG. 1D illustrates a top view of the nanogap in the nanodevice according to an embodiment.

FIG. 2A is a picture via a transmission electron microscope (TEM) of a nanowire according to an embodiment.

FIG. 2B is a TEM picture of a first nanogap cut by a helium ion beam under certain conditions according to an embodiment.

FIG. 2E is a TEM picture of a unique signature surrounding the nanogap according to embodiment.

FIG. 4C illustrates an enlarged, partial top view of the nanodevice showing a bridge according to an embodiment.

FIG. 4D illustrates the enlarged, partial top view of the nanodevice in which the bridge is cut forming the two extensions according to an embodiment.

FIG. 6 is a flow diagram illustrating a method for manufacturing a nanogap of the nanodevice in the nanowire according to an embodiment.

FIG. 7 is a flow diagram illustrating a method for manufacturing nanogaps in the nanowire of the nanodevice according to an embodiment.

FIG. 8 is a block diagram that illustrates an example of a computer (computer test setup) having capabilities, which may be included in and/or combined with embodiments.

DETAILED DESCRIPTION

Figure 2C:
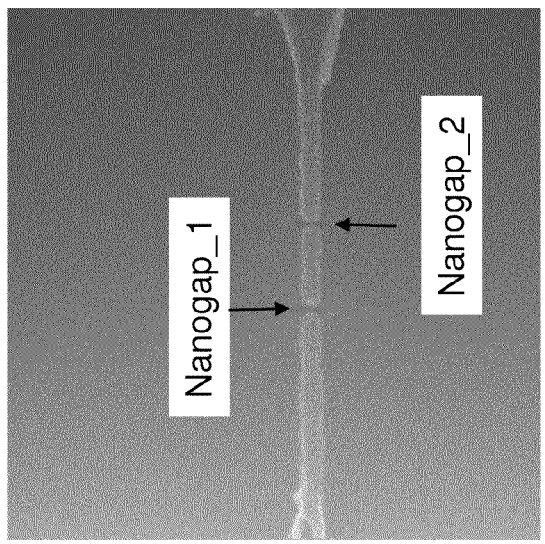
FIG. 2C is a TEM picture of a second nanogap cut by a helium ion beam under certain conditions according to an embodiment.

The fabrication of a sub-3 nm gap between two palladium electrodes has been pursued to create a device capable of recognizing individual DNA bases by tunneling current measurements. This base recognition device is the key component of generation 4 single molecule sequencing technology. Towards this end, several approaches have been proposed or pursued to achieve a sub-3 nm gap between electrodes, such as a focused transmission electron microscope (TEM) beam cutting, or scanning tunneling microscope electrodes. The primary problem with all of these solutions is that none of them provides a clear cut path to scaling up (manufacturing) production of the tunneling devices. Reproducibility or consistency of the nanogaps at these dimensions has also been a challenge. Importantly, manufacturing approaches commonly used to achieve high-fidelity nanoscale features like electron beam (e-beam) lithography can be inadequate to realize the needed gap sizes.

Embodiments are configured to use a focused helium beam to mill through palladium (Pd) nanowires to fabricate sub-3 nm gap devices for DNA base recognition. Dividing a continuous palladium nanowire in this way to create two separate palladium electrodes provides a high throughput and reproducible path for sub-3 nm gap creation with a unique and identifiable process signature. The focused helium beam method also permits tapering of the nanowire to enhance tunneling recognition capabilities. For example, the electrodes can be sharpened to a finer tip closer to the gap to reduce the probability of tunneling signatures originating from multiple bases simultaneously. In addition, the helium beam cutting method can be applied to any substrate in contrast to the TEM approach, which is confined to globally or locally thin substrates.

FIG. 1A illustrates a cross-sectional view of a method of forming a nanogap in a nanodevice 100 according to an embodiment. The nanodevice 100 has an electrically insulating substrate 102 which may be a silicon wafer. An oxide layer 104 may be deposited (e.g., grown) on the substrate 102. The oxide layer 104 is a dielectric material, and may be any dielectric material including silicon dioxide.

A nanowire 106 is deposited on the oxide layer 104. FIG. 1B illustrates a top view of the nanodevice 100. The material of the nanowire may be palladium. The palladium nanowires 106 can be fabricated on the dielectric oxide layer 104 using, for example, e-beam lithography and lift-off. The nanowires 106 can also be defined by optical lithography and reactive ion etching. The width W of the nanowires 106 may range from a few nanometers to micrometers (e.g., 3 nm to 8 μm) and the thickness T may vary from 2 nm to 50 nm.

With the palladium nanowire 106 in place, a helium ion microscope 120 with a focused He ion beam is used to controllably create sub-3 nm gaps by varying the exposure conditions. FIG. 1C illustrates a cross-sectional view of a sub-3 nm nanogap 110 cut in the nanowire 106, while FIG. 1D illustrates a top view of the nanogap 110. The cutting by the helium microscope 120 results in palladium electrode 106A (e.g., left nanowire electrode) and palladium electrode 106B (e.g., right nanowire electrode) which together form the nanowire 106. The width of the nanogap 110 is shown by D1. The width D1 of the nanogap 110 is formed to be less than 3 nanometers (e.g., 1 or 2 nm) via He ions irradiated from the helium ion microscope 120. Similar to an electron microscope, one skilled in the art understands the operation of the helium ion microscope 120 at discussed herein.

An example of commercially available helium ion microscopes are the ORION™ Helium ion Microscope from Carl Zeiss SMT and the Multiple Ion Beam Microscopes from Carl Zeiss SMT.

The following example shows the gap cutting conditions of the helium ion microscope 120 for palladium nanowires 106 with specific dimensions in which the width is approximately (~) 20 nm and the thickness is approximately 10 nm (where the thickness is 1 nm Ti and 9 nm Pd). In the example exposure conditions (to control the helium ion microscope 120), the beam current is 0.4 pA (picoamperes), the beam spot size is 3.4 to 5 Å (angstroms), the step size is 5 Å, the working distance may be 7.354 mm (millimeters), and the aperture (opening) is 5 μm.

Figure 2D:
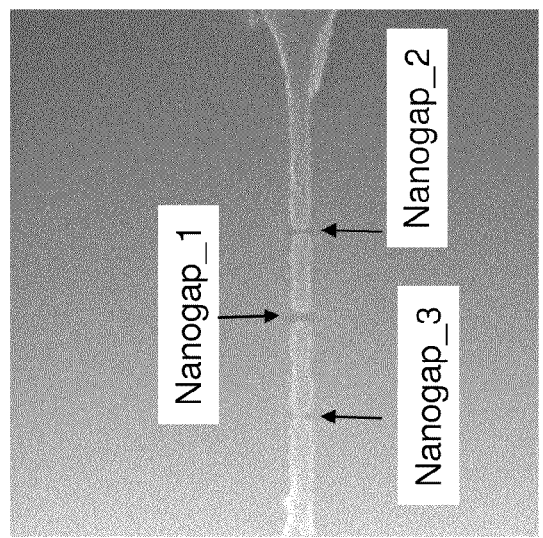
FIG. 2D is a TEM picture of a third nanogap cut by a helium ion beam under certain conditions according to an embodiment.

By varying parameters (in the helium ion microscope 120) such as the exposure time per pixel, a nanogap can be reproducibly fabricated with a distance (D1) less than 3 nm. At 30 kV (kilovolts), 2 μs/pixel (exposure time) on a 15 nm wide and 10 nm thick palladium nanowire (line) in FIG. 2A yields a 4 nm gap (e.g., nanogap_1) in FIG. 2B. By reducing the exposure time per pixel, the width of the gap can be made smaller. In this case, a 1 μs/pixel exposure time generates a 3 nm gap (nanogap_2) shown in FIG. 2C, and 0.5 μs/pixel exposure time generates a gap (nanogap_3) (e.g., between 1 and 3 nm) that is below the resolution of the helium microscope shown in FIG. 2D.

Figure 2G:
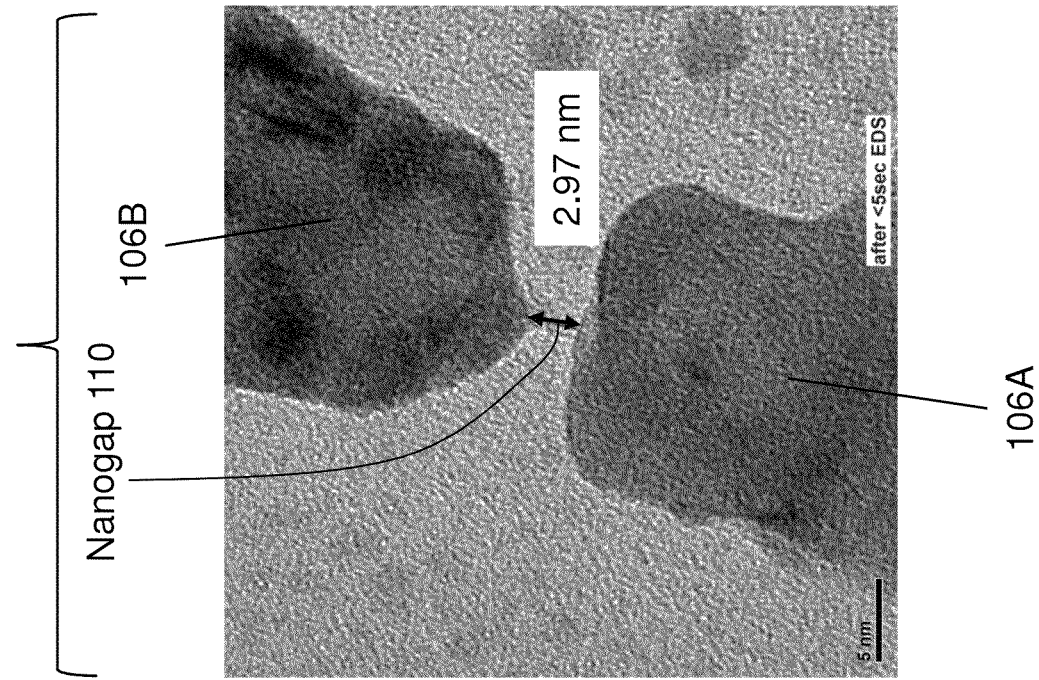
FIG. 2G is a TEM picture of the nanogap with the residual palladium removed according to an embodiment.

Note that in FIGS. 2A, 2B, 2C, and 2D (along with FIGS. 2E through 2G) the evaporated palladium lines (i.e., nanowires 106) are cut by a focused helium beam, and the resulting gaps are respectively shown by the arrows pointing to nanogap_1, nanogap_2, and nanogap_3. FIG. 2E reveals electrode nanogaps of less than 3 nm (e.g., 2.77 nm). Also, as seen in FIG. 2E, use of the helium ion beam provides a unique signature according to an embodiment. Note the (unique) signature splash of palladium particles/dots 205 surrounding the nanogap is a result of He ion beam exposure according to embodiments. The palladium dots 205 may have sizes ranging from 2 to 8 nm in diameter. The palladium dots 205 surrounding the nanogap 110 are not observed with TEM cutting on thin membranes (i.e., thin electrodes).

Figure 2F:
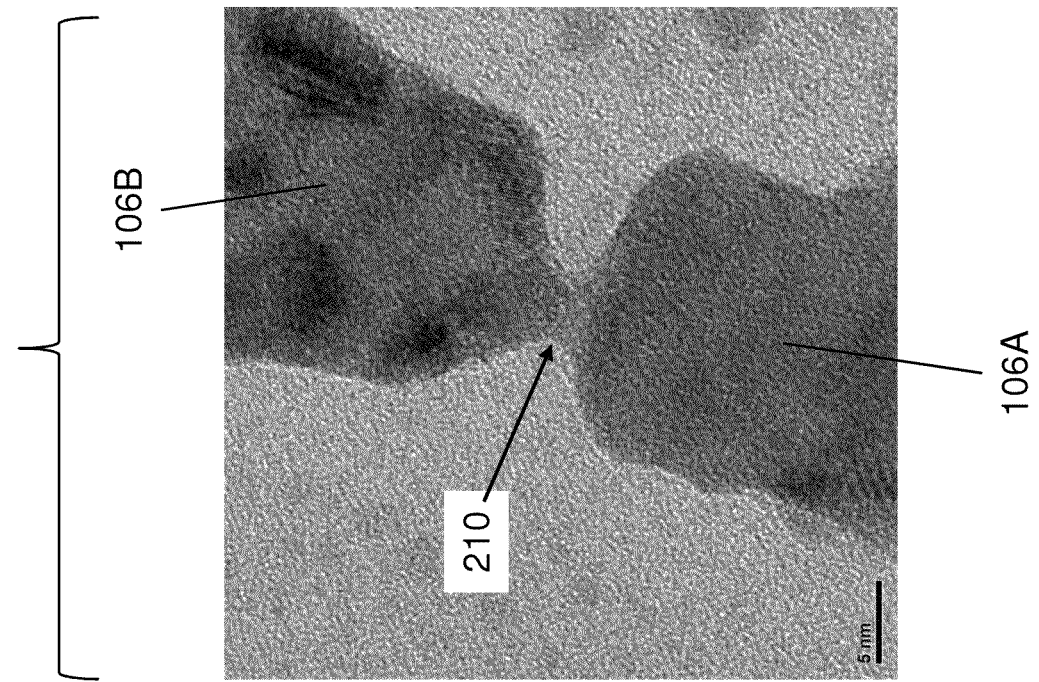
FIG. 2F is a TEM picture of the nanogap with residual palladium according to an embodiment.

FIG. 2F shows one palladium gap with residual palladium 210 still connecting (i.e., bridging) the electrodes 106A and 106B after cutting with the helium ion beam. In this case, the focusing of the electron beam in the TEM (or He ion beam) is used to remove the residual palladium 210 yielding the nanogap 110 shown in FIG. 2G. The nanogap 110 is 2.97 nm. The structures in FIGS. 2A through 2G were imaged with high resolution transmission electron microscopy (TEM).

Figure 3A:
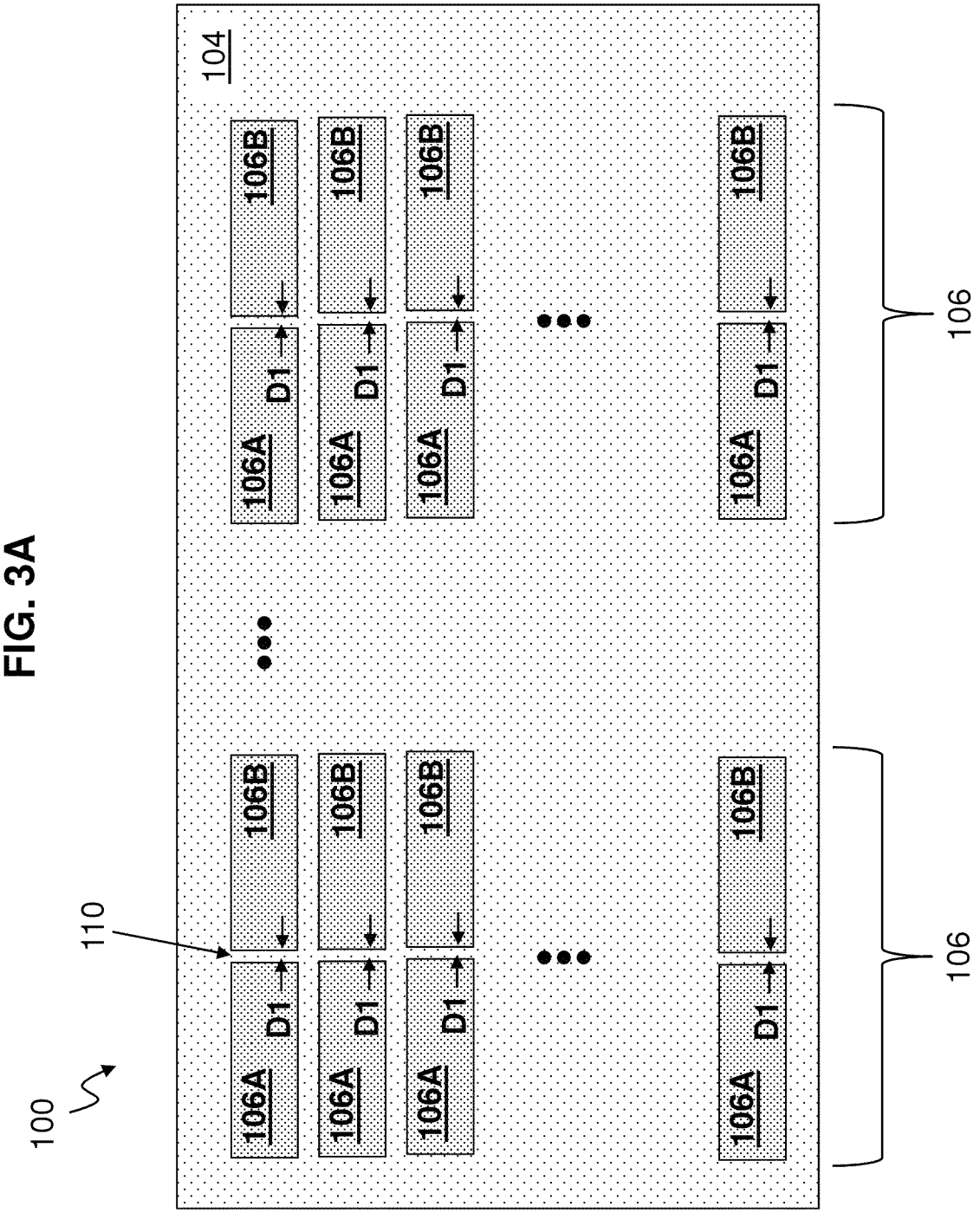
FIG. 3A schematically illustrates an array of nanodevices each having a nanogap formed by the helium ion beam according to embodiments.
Figure 3B:
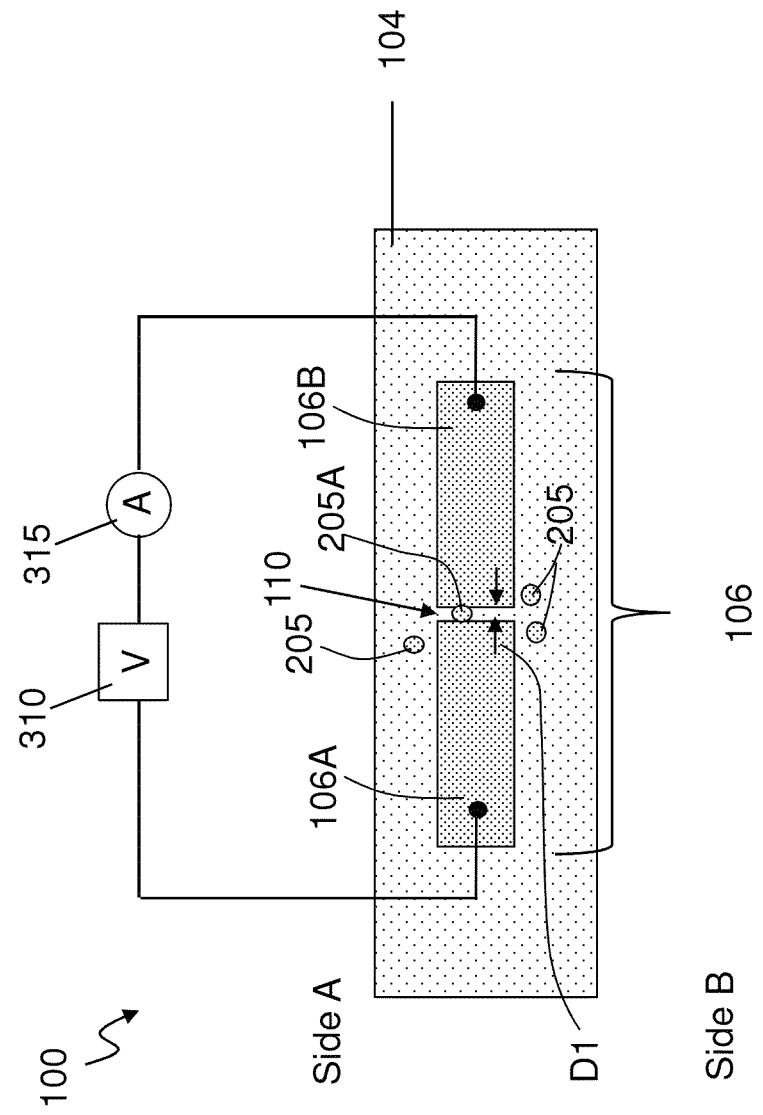
FIG. 3B schematically illustrates testing each individual nanodevice in the array to determine whether residual palladium is in the nanogap according to embodiments.

FIG. 3A illustrates an array of nanodevices 100 each having a nanogap 110 formed by the helium ion beam of the helium ion microscope 120 according to embodiments. FIG. 3B illustrates how each individual nanodevice 100 may be tested to determine if there is residual palladium dot/particle 205 in the gap 110 between electrodes 106A and 106B. Voltage of voltage source 310 is applied to the electrodes 106A and 106B to generate a current measured by an ammeter 315, and the amount of current determines if there is a residual palladium particle 205 in the gap 110. Assume that there is a residual particle 205A bridging (i.e., physically and/or electrically connecting) the electrode 106A to electrode 106B, and in such a case, the measured current by ammeter 315 may be nanoamperes to microamperes because of the residual particle 205A. If no residual particle 205A is present (in gap 110) between electrode 106A and electrode 106B, the measured current may be in the range of 200 pA at 400 mV bias.

When it is determined during manufacturing that residual particles 205A are connecting the two electrodes 106A and 106B, there are two options. The occasional nanodevices 100 having the residual particles 205A in the gap 110 may be discarded, while the remaining nanodevices 100 in the array on the wafer 102 are utilized for sequencing as discussed herein. Alternatively and/or additionally, the nanodevices 100 having the residual particle 205A may be further treated with an electron beam of a transmission electron microscope (and/or He ion beam) in the gap 110 to clear the residual particle 205A. Removing the residual particle 205A with the electron beam results in the clear nanogap 110 shown in FIGS. 1C and 1D. Out of the array of nanodevices 100 on the wafer 102, there may be only a few nanodevices 100 that have the residual particle 205A remaining in the gap 110, and the residual particle 205A is cut (removed) by the electron beam of the transmission electron microscope even though the gap 110 has already been (originally) cut using the helium ion beam of the helium ion microscope 120.

Cutting a sub-3 nm gap with an electron beam (from start to finish) requires an enormous amount of time and skill as compared with a helium ion beam. Therefore, even if a few (e.g., 15%) out of an array of nanodevices 100 on wafer 102 have a residual particle 205A in the gap 110 (originally cut by the helium ion beam), the time to then remove the residual particle 205A using the electron beam (for the few nanodevices 100) is much less than the time required to cut gaps for an array of nanodevices using the electron beam. TEM requires sample mounting (i.e., nanodevice 100 mounting) and high vacuum which takes up to 30 minutes (min) for any given sample inserted in the TEM. Then, each gap takes about 20 min to cut exclusively by TEM. The TEM touch up of previously He beam cut gaps only requires a few milliseconds of beam exposure to remove residual Pd (e.g., from the nanogap 110).

Figure 4A:
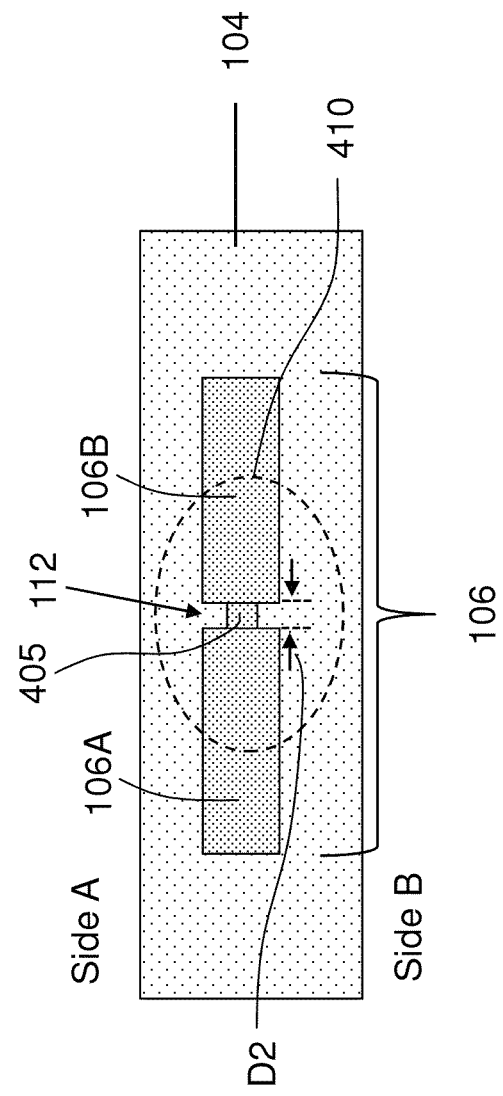
FIG. 4A illustrates a top view of the nanodevice in which the nanowire is intentionally tapered by the helium ion beam according to an embodiment.

FIG. 4A illustrates a top view of the nanodevice 100 in which the nanowire 106 has been intentionally tapered by the He ion beam in the vicinity of the nanogap 112 according to an embodiment. The helium ion microscope 120 is controlled to cut the nanowire laterally on side A and side B without cutting completely through the nanowire 106. This intentionally leaves a palladium bridge 405 connecting the left electrode 106A to the right electrode 106B. The nanogap 112 is cut with a width D2 that is larger than the width D1.

Figure 4B:
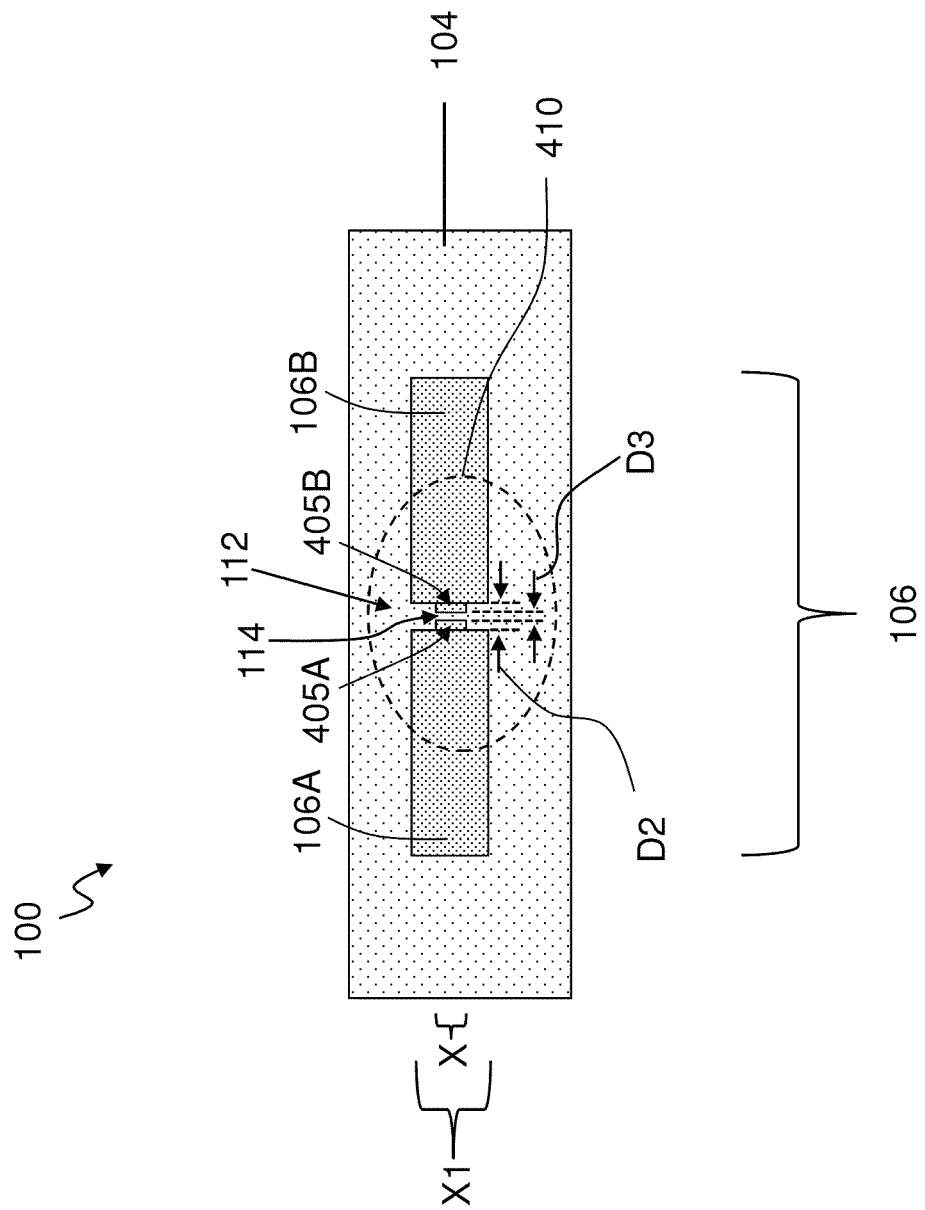
FIG. 4B illustrates a top view of the nanodevice with left and right extensions respectively extending from left and right electrodes to form a second nanogap according to an embodiment.

The helium ion microscope 120 (and/or an electron microscope) is controlled to cut a smaller nanogap 114 in the palladium bridge 405 resulting in extension 405A and extension 405B in FIG. 4B. FIG. 4B illustrates a top view of the nanodevice 100 with left extension 405A extending from and as part of electrode 106A, and with right extension 405B extending from and as part of electrode 106B. The newly formed nanogap 114 has a width that may equal and/or be less than the width D1 of nanogap 110. The width D2 of the nanogap 112 may be 4 to 10 nm and the width of the smaller nanogap D3 (formed between extensions 405A and 405B) may be, e.g., 0.3, 0.4, 0.5, 0.7, . . . 1 through 2 nm (to fit/accommodate the diameter (size) base/nucleotide to be sequenced). By having a larger nanogap 112 (D2) during DNA sequencing, the larger nanogap 112 ensures that multiple DNA bases are not interacting with the electrodes 106A and 106B because the distance (D2) between the electrodes 106A and 106B (e.g., 7 nm or more) is too large for tunneling current to travel. As understood by one skilled in the art, the DNA is moved into nanogap 114 between the extensions 405A and 405B (of the respective electrodes 106A and 106B). The dimension X of the extensions 405A and 405B may be made to accommodate a single base in the nanogap 114. For example, the dimension X has a distance smaller than the separation/spacing between bases of the molecule being tested. The distance X of the extensions 405A and 405B may be 3, 4, 5, 6, 7 angstroms depending on (base separation distance of) the target molecule being sequenced. Therefore, if the distance X is 3.5 Å, the nanogap 114 between extensions 405A and 405B can (only) have a single base at a time and the measured tunneling current can identify the particular base presently in the nanogap 114 without simultaneously measuring tunneling current from neighboring bases that may be in the larger nanogap 112. The dimension X1 of the nanowire 106 may be 20.

Figure 4E:
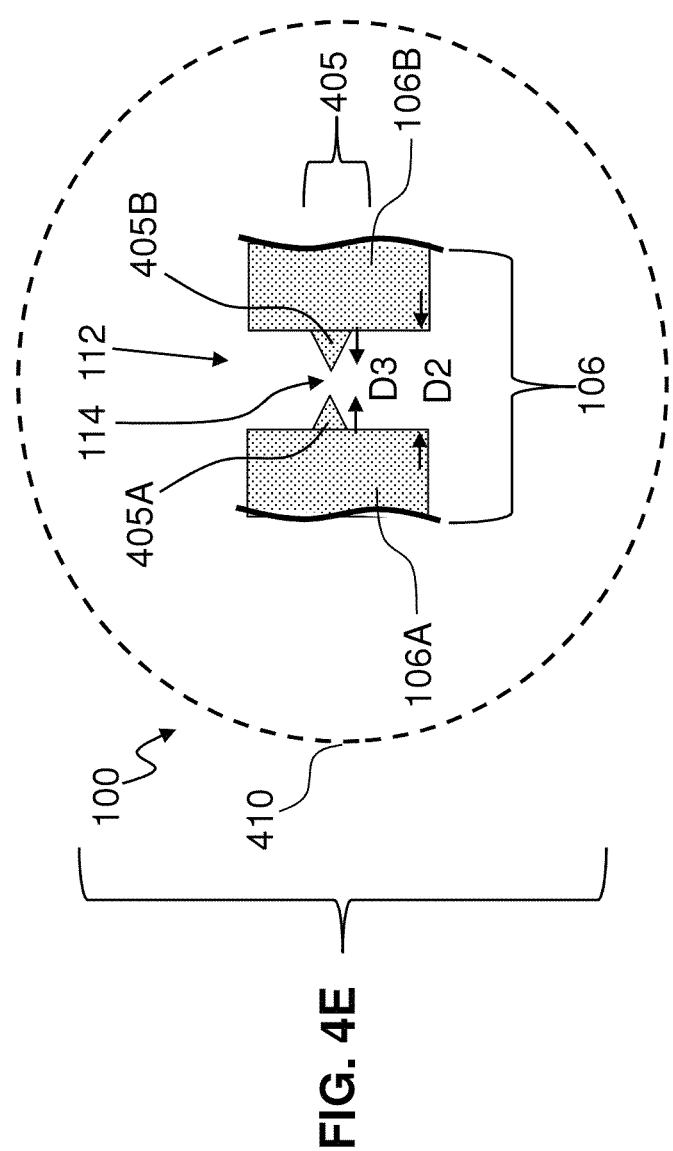
FIG. 4E illustrates another enlarged, partial top view of the nanodevice with the two extensions according to an embodiment.

In FIGS. 4A and 4B, view 410 is a dashed circle of an enlarged portion shown in FIGS. 4C, 4D, and 4E. The views 410 in FIGS. 4C, 4D, and 4E are partial views; the substrate 102 and oxide 104 are not shown so as not to obscure the figures.

FIG. 4C illustrates a partial top view of the nanodevice 100 in which the palladium bridge 405 is shown as rounded portions (physically and electrically) connecting the left and right electrodes 106A and 106B in the nanogap 112. FIG. 4D illustrates the partial top view of the nanodevice 100 in which the palladium bridge 405 has been further cut (via the helium ion beam and/or electron beam of the helium ion microscope 120) into the two separate extensions 405A and 405B (shown as rounded portions extending from electrodes 106A and 106B). This results in the smaller nanogap 114 only between extensions 405A and 405B.

FIG. 4E illustrates the partial top view of the nanodevice 100 in which the two extensions 405A and 405B are shown as triangular shaped portions extending from electrodes 106A and 106B according to an embodiment. The nanogap 114 is between the triangular shaped portions.

Figure 5A:
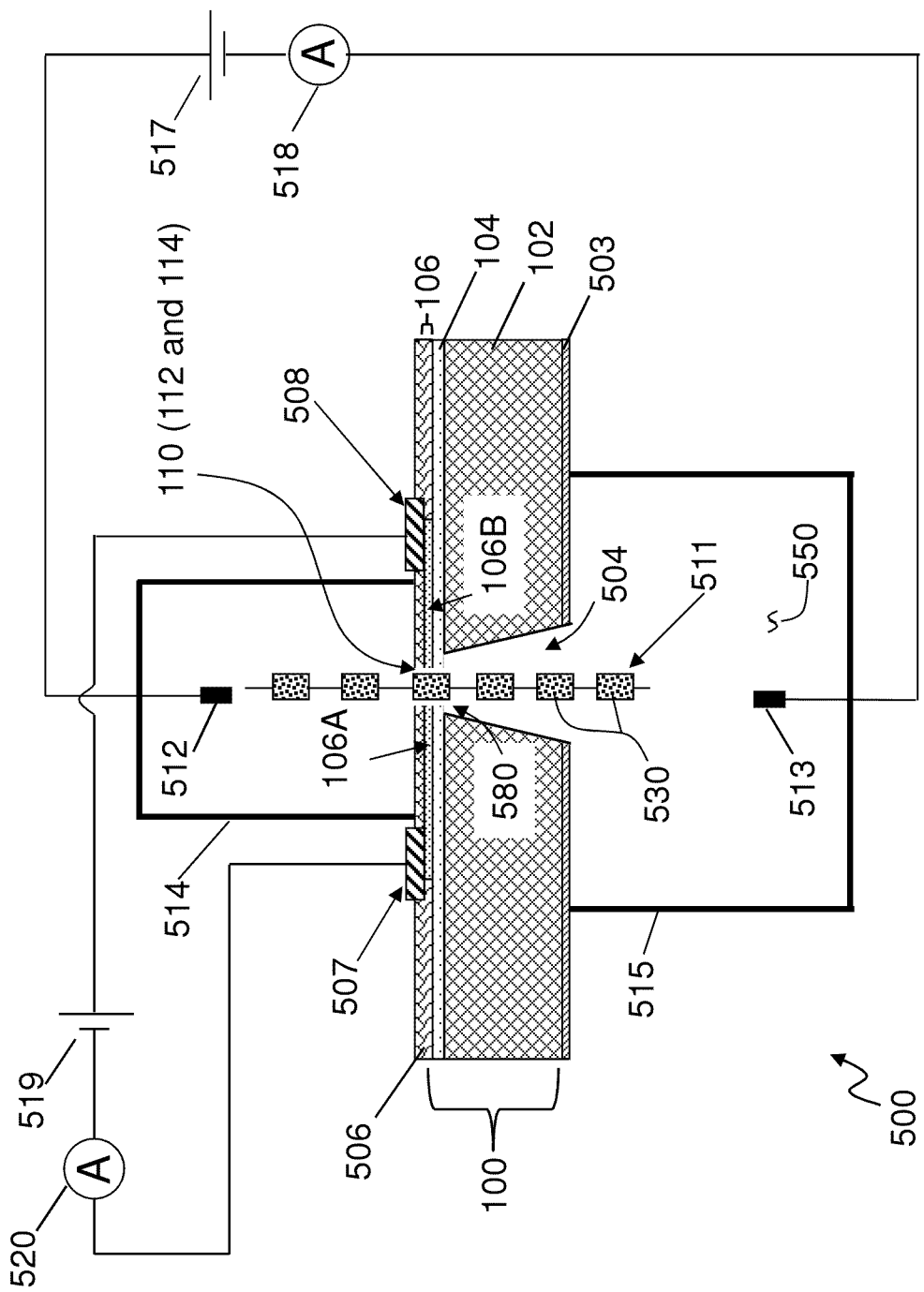
FIG. 5A illustrates a sequencing system utilizing the nanodevice according to an embodiment.
Figure 5B:
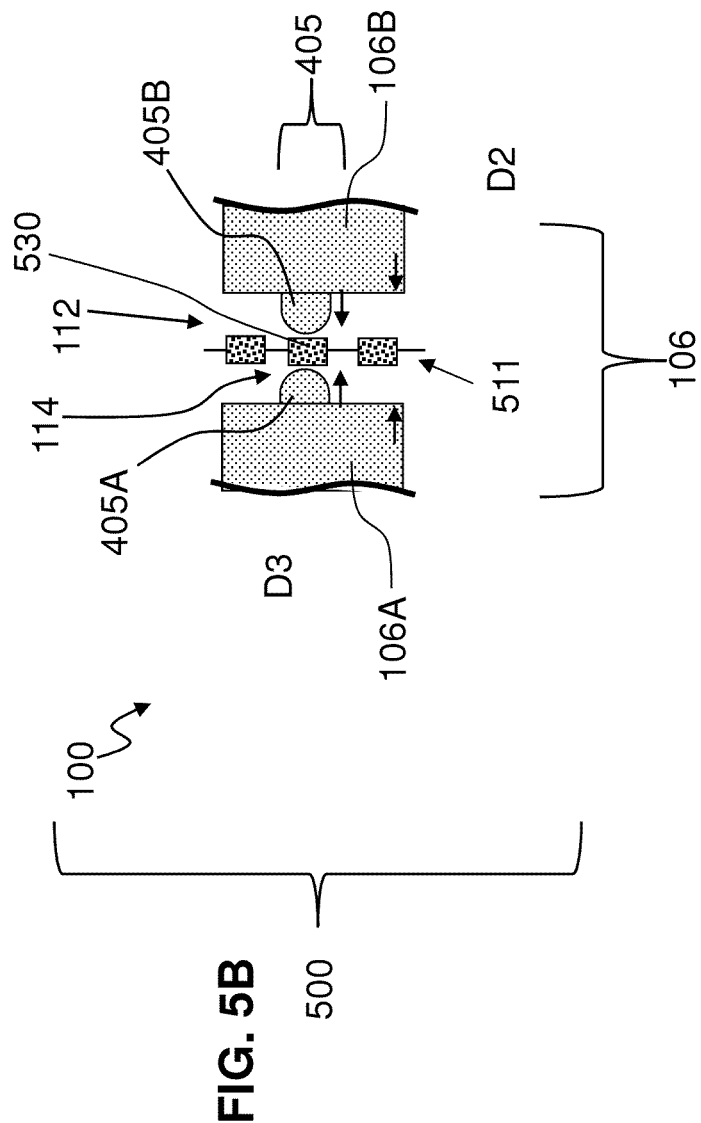
FIG. 5B illustrates an enlarged, partial view of the system showing the two extensions according to an embodiment.

FIG. 5A illustrates a system 500 for sequencing using the nanodevice 100 according to an embodiment. As discussed above, the nanodevice 100 includes the electrically insulating substrate 102 (wafer), oxide 104, electrodes 106A and 106B (with respective extensions 405A and 405B not shown for the sake of clarity), and nanogap 110 (or nanogaps 112 and 114).

The system includes electrically insulating films 503 and 506. A backside cavity 504 forms a suspended membrane making up the nanogap 110 (nanogap 112 and 114). The electrodes 507 and 508 are metal contact pads, which may be any metal.

In the system 500, a top reservoir 514 is attached and sealed to the top of the insulating film 506, and a bottom reservoir 515 is attached and sealed to the bottom of the insulating film 503. Electrode 512 is in the top reservoir 514, and electrode 513 is in the bottom reservoir 515. Electrodes 512 and 513 may be silver/silver chloride, or platinum for example. The reservoirs 514 and 515 are the inlet and outlet respectively for buffer solution 550, and reservoirs 514 and 515 hold the DNA and/or RNA samples for sequencing. The buffer solution 550 is an electrically conductive solution (such as an electrolyte) and may be a salt solution such as NaCl.

The system 500 shows a target molecule 511, which is the molecule being analyzed and/or sequenced. As an example DNA sample, the system 500 may include a single stranded DNA molecule 511, which is passing through the nanogap 110 (nanogaps 112 and 114). The DNA molecule 511 has bases 530 (A, G, C, and T) represented as blocks.

The DNA molecule 511 is pulled through the nanogap 110 (nanogaps 112 and 114) by a vertical electrical field generated by the voltage source 517. When voltage is applied to electrodes 512 and 513 by the voltage source 517, the voltage generates the electric field (between reservoirs 514 and 515) that controllably (e.g., by turning on and off the voltage source 517) drives the DNA molecule 511 into and through the nanogap 110 (nanogaps 112 and 114). Also, the voltage of the voltage source 517 can produce the gate bias between electrodes 507 and 508. Note that the electrodes 507, 508, 106A, and 106B, nanogap 110 (114) may operate as a transistor. The voltage across the nanogap 110 (nanogaps 112 and 114) from the voltage source 517 can be the gate for controlling the transistor. Metal pads (electrodes) 507 and 508 are the drain and source respectively for the transistor device. Voltage applied by voltage source 519 to electrodes 507 and 508 also builds the electrical field, which can hold the base 530 in the nanogap 110 for sequencing. Note that metal pads 507 and 508 are electrically connected to electrodes 106A and 106B having the nanogap 110 (nanogaps 112 and 114).

Note that a nanopore 580 is formed in layers 506 and 104 which is larger than the nanogap 110 (112 and 114). The nanogap 110 (112 and 114) is in the nanopore 580. The nanopore 580 connects top reservoir 514 to bottom reservoir 515 as understood by one skilled in the art. Ammeter 518 monitors the ionic current change when DNA (or RNA) molecule 511 goes through nanogap 110 (112 and 114) (which is within the nanopore 580). The ionic current (measured by the ammeter 518) flows through electrode 512, into the buffer solution 550, through the nanopore 580 (to interact with the base 530 when the target molecule 511 is present in the nanopore 580), out through the electrode 513. Voltage generated by the voltage source 519 produces the voltage between source 508 and drain 507. Another ammeter 520 monitors the source-drain transistor current from nanogap 110 (112 and 114) (of the transistor through the buffer solution 550) to detect nucleotide (i.e., base) information when the DNA/RNA molecule 511 passes through the nanogap 110 (112 and 114).

For example, when a base 530 is in the nanopore 580 (between the nanogap 110 (or nanogaps 112 and 114) of the nanowire 106) and when voltage is applied by the voltage source 519, source-drain transistor current flows to source 508, into the right nanowire electrode 106B, into the buffer solution 550 (between the nanogap) to interact with the base 530 positioned therein, into left nanowire electrode 106A, out through the drain 507, and to the ammeter 520. The ammeter 520 is configured to measure the change in source-drain current when each type of base 530 is present in the nanogap 110 (nanogaps 112 and 114) (between the left and right electrodes 106A and 106B) and also when no base 530 (of the DNA molecule 511) is present. The respective bases 530 are determined by the amplitude of the source-drain transistor current when each respective base in present in the nanogap 110 (or nanogaps 112 and 114) of the nanopore 580. As discussed for FIGS. 4B, 4D, and 4E, FIG. 5B illustrates a partial view of the system 500 with extensions 405A and 405B extending from electrodes 106A and 106B respectively. The single base is (only) within the nanogap 114 although other bases 530 may be in the larger nanogap 112.

When the single base 530 is present in the nanogap 114 and when voltage is applied by the voltage source 519, source-drain transistor current flows to source 508, into the right nanowire electrode 106B, into right extension 405B, into the buffer solution 550 (between the nanogap 114) to interact with the base 530 positioned therein, into left extension 405A, into left nanowire electrode 106A, out through the drain 507, and to the ammeter 520. The ammeter 520 is measure the tunneling current (source-drain current) when the base 530 is present in the nanogap 114. This same process occurs for the rectangular and triangular shaped extensions 405A and 405B shown in FIGS. 4B and 4E.

FIG. 6 illustrates a method for manufacturing a nanogap in the nanowire 106 (of the nanodevice 100) which can be utilized for DNA, RNA sequencing according to an embodiment. Reference can be made to FIGS. 1-5 discussed herein.

An oxide 104 is disposed (e.g., grown) on top of a substrate 102 (wafer) at block 605, and the nanowire 106 is disposed on top of the oxide 104 at block 610. The lift-off process may be utilized to dispose and pattern the metal of the nanowire 106. As understood by one skilled in the art a positive resist process or a negative resist process may be utilized to dispose and pattern the nanowire 106.

A helium ion beam is applied via the helium ion microscope 120 to cut the nanowire 106 into a first nanowire part (e.g., electrode 106A) and a second nanowire part (e.g., electrode 106B) to form the nanogap 110 in the nanodevice 100 at block 615.

When the helium ion beam is applied (via the helium ion microscope 120) to cut the nanogap 110, a signature of nanowire material (e.g., palladium particles/dots 205) is formed in the proximity to the openings of the nanogap 110 (e.g., as shown in FIGS. 2E and 3B) at block 620.

The signature of the nanowire material comprises nanowire material particles (e.g., palladium particles/dots 205) in proximity to the openings of the nanogap 110 as a result of the helium ion beam. The He beam energy vaporizes the palladium which may redeposit in round droplets when the He beam is switched off.

As a result of applying the helium ion beam, voltage is applied by the voltage source 310 to determine that a nanowire material particle (i.e., palladium particle 205A) is lodged in the nanogap 110 in which the nanowire material particle connects the first nanowire part and the second nanowire part (i.e., connects electrode 106A to electrode 106B). When it is determined that the nanowire material particle is lodged in the nanogap 110, the nanowire material particle in the nanogap 110 is removed by applying an electron beam and/or a helium ion beam. Note that the helium ion microscope 120 may be configured to irradiate both electron beams and helium ion beams as desired. Alternatively and/or additionally, when it is determined that the nanowire material particle is lodged in the nanogap 110, the particular nanodevice 100 having the nanowire particle lodged in the nanogap 110 out of an array of good nanodevices 100 (shown in FIG. 3A) having nanogaps 110 (with no lodged palladium particles 205 as determined in FIG. 3B).

The nanowire 106 may be (only) palladium and/or other metals. The substrate/wafer 102 may be silicon, germanium, etc. The oxide 104 may be silicon dioxide, and/or other dielectric materials.

FIG. 7 illustrates a method for manufacturing nanogaps 112 and 114 (which may be the same as nanogap 110) in the nanowire 106 (of the nanodevice 100) which can be utilized for DNA, RNA sequencing according to an embodiment. Reference can be made to FIGS. 1-5 discussed herein.

An oxide 104 is disposed (e.g., grown) on top of a substrate 102 (wafer) at block 705, and the nanowire 106 is disposed on top of the oxide 104 at block 710. The lift-off process may be utilized to dispose and pattern the metal of the nanowire 106.

As understood by one skilled in the art a positive resist process or a negative resist process may be utilized to dispose and pattern the nanowire 106.

A helium ion beam is applied via the helium ion microscope 120 to taper the nanowire 106 laterally (e.g., on side A and side B but not in between) into a first nanowire part (e.g., electrode 106A in FIG. 4A) and a second nanowire part (e.g., electrode 106B), where the first nanowire part and the second nanowire part form a first nanogap (e.g., nanogap 112) in the nanodevice 100 at block 715.

Applying the helium ion beam to taper the nanowire laterally intentionally forms a bridge 405 connecting the first nanowire part (electrode 106A) and the second nanowire part (electrode 106B) at block 720.

Further applying the helium ion beam and/or an electron beam cut a second nanogap (e.g., nanogap 114) in/through the bridge 405 to form a first extension (e.g., extension 405A) from/on the first nanowire part (electrode 106A) and form a second extension (e.g., extension 405B) from/on the second nanowire part (electrode 106B) at block 725.

The second nanogap 114 is thinner than the first nanogap 112 (i.e., D3<D2). The nanowire 106 is tapered in order for the first extension 405A and the second extension 405B to have rectangular shapes after the second nanogap 114 is cut as shown in FIGS. 4A and 4B. The nanowire 106 is tapered in order for the first extension 405A and the second extension 405B to have rounded shapes after the second nanogap 114 is cut as shown in FIGS. 4C and 4D. The nanowire 106 is tapered in order for the first extension 405A and the second extension 405B to have triangular shapes after the second nanogap 114 is cut as shown in FIG. 4E.

The second nanogap 114 is formed by (i.e., is in between) the first extension 405A and the second extension 405B. The size (e.g., the distance X of the extensions 405A and 405B) of the second nanogap 114 accommodates a single base or a single nucleotide of the target molecule 511 in which the target molecule 511 may include a deoxyribonucleic acid molecule, a ribonucleic acid molecule, and/or a protein that is to be sequenced in the system 500. The size of the second nanogap 114 allows (only) the single base or the single nucleotide to be sequenced via a measured current (of ammeter 520) while in the second nanogap 114 between the first and second extensions.

The first extension 405A and the second extension 405B both extend into the first nanogap 112.

FIG. 8 illustrates an example of a computer 800 (e.g., as part of the computer test setup for testing and analysis) which may implement, control, and/or regulate the respective voltages of the voltage sources, respective measurements of the ammeters, and display screens for displaying various current amplitude (including ionic current and transistor (source to drain current)) as discussed herein. The computer 800 also stores the respective electrical current amplitudes of each base tested and measured to be compared against the baselines current amplitudes of different bases, which is utilized to identify the bases of the tested/target molecule.

Various methods, procedures, modules, flow diagrams, tools, applications, circuits, elements, and techniques discussed herein may also incorporate and/or utilize the capabilities of the computer 800. Moreover, capabilities of the computer 800 may be utilized to implement features of exemplary embodiments discussed herein. One or more of the capabilities of the computer 800 may be utilized to implement, to connect to, and/or to support any element discussed herein (as understood by one skilled in the art) in FIGS. 1-7. For example, the computer 800 which may be any type of computing device and/or test equipment (including ammeters, voltage sources, current meters, connectors, etc.). Input/output device 870 (having proper software and hardware) of computer 800 may include and/or be coupled to the nanodevices and structures discussed herein via cables, plugs, wires, electrodes, patch clamps, etc. Also, the communication interface of the input/output devices 870 comprises hardware and software for communicating with, operatively connecting to, reading, and/or controlling voltage sources, ammeters, and current traces (e.g., magnitude and time duration of current), etc., as discussed and understood herein. The user interfaces of the input/output device 870 may include, e.g., a track ball, mouse, pointing device, keyboard, touch screen, etc., for interacting with the computer 800, such as inputting information, making selections, independently controlling different voltages sources, and/or displaying, viewing and recording current traces for each base, molecule, biomolecules, etc.

Generally, in terms of hardware architecture, the computer 800 may include one or more processors 810, computer readable storage memory 820, and one or more input and/or output (I/O) devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a data signal processor (DSP), or an auxiliary processor among several processors associated with the computer 800, and the processor 810 may be a semiconductor based microprocessor (in the form of a microchip) or a macroprocessor.

The computer readable memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the computer readable memory 820 may include one or more separate programs, each of which comprises an ordered listing of executable instructions for implementing logical functions. The software in the memory 820 includes a suitable operating system (O/S) 850, compiler 840, source code 830, and one or more applications 860 of the exemplary embodiments. As illustrated, the application 860 comprises numerous functional components for implementing the features, processes, methods, functions, and operations of the exemplary embodiments.

The operating system 850 may control the execution of other computer programs, and provides scheduling, input-output control, file and data management, memory management, and communication control and related services.

The application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as (a) an object oriented programming language, which has classes of data and methods, or (b) a procedure programming language, which has routines, subroutines, and/or functions.

The I/O devices 870 may include input devices (or peripherals) such as, for example but not limited to, a mouse, keyboard, scanner, microphone, camera, etc. Furthermore, the I/O devices 870 may also include output devices (or peripherals), for example but not limited to, a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or an intranet. The I/O devices 870 may be connected to and/or communicate with the processor 810 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 860 is implemented in hardware, the application 860 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A structure utilized in sequencing, the structure comprising:
   an oxide on a wafer;
   a nanowire on the oxide;
   a first nanowire part and a second nanowire part formed of the nanowire, wherein the first nanowire part and the second nanowire part are separate and directly opposite from one another to form a first nanogap;
   wherein the first nanowire part and the second nanowire part have straight portions opposing to and parallel to one another that form the first nanogap;
   wherein the first nanogap is defined between the straight portions of the first nanowire part and the second nanowire part;
   wherein the first nanogap ranges from 4 to 10 nanometers;
   a first extension attached to and extending from the straight portion of the first nanowire part;
   a second extension attached to and extending from the straight portion of the second nanowire part, wherein the first extension and the second extension extend toward each other;
   a second nanogap formed between the first extension and the second extension;
   wherein the second nanogap is structured for a target molecule to pass between the first extension and the second extension having formed the second nanogap.

2. The structure of claim 1, wherein the second nanogap is thinner than the first nanogap.

3. The structure of claim 1, wherein the nanowire is tapered in order for the first extension and the second extension to have rectangular shapes after the second nanogap is cut.

4. The structure of claim 1, wherein the nanowire is tapered in order for the first extension and the second extension to have rounded shapes after the second nanogap is cut.

5. The structure of claim 1, wherein the nanowire is tapered in order for the first extension and the second extension to have triangular shapes after the second nanogap is cut.

6. The structure of claim 1, wherein the second nanogap is smaller than the first nanogap.

7. The structure of claim 1,
   wherein the second nanogap ranges from 0.3 to 1 nanometer.

8. The structure of claim 1, further comprising:
   a first reservoir; and
   a second reservoir, the second nanogap connecting the first reservoir to the second reservoir.

9. The structure of claim 1, wherein the first extension of the first nanowire part is tapered; and
   wherein the second extension of the second nanowire part is tapered.

* * * * *